US008251966B2

(12) United States Patent
Kudo et al.

(10) Patent No.: US 8,251,966 B2
(45) Date of Patent: Aug. 28, 2012

(54) ABSORPTIVE ARTICLE

(75) Inventors: Jun Kudo, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 664 days.

(21) Appl. No.: 12/307,109

(22) PCT Filed: Jul. 5, 2007

(86) PCT No.: PCT/JP2007/063505
§ 371 (c)(1),
(2), (4) Date: Dec. 30, 2008

(87) PCT Pub. No.: WO2008/004637
PCT Pub. Date: Jan. 10, 2008

(65) Prior Publication Data
US 2010/0145296 A1 Jun. 10, 2010

(30) Foreign Application Priority Data
Jul. 5, 2006 (JP) ................................ 2006-186142

(51) Int. Cl.
*A61F 13/15* (2006.01)
*A61F 13/20* (2006.01)
(52) U.S. Cl. ........ 604/385.01; 604/385.101; 604/385.04
(58) Field of Classification Search ............. 604/385.01, 604/385.101
See application file for complete search history.

(56) References Cited

U.S. PATENT DOCUMENTS

| 4,022,210 | A | * | 5/1977 | Glassman | ..................... 604/394 |
| 4,770,657 | A | * | 9/1988 | Ellis et al. | ................. 604/385.31 |
| 5,624,421 | A | * | 4/1997 | Dabi et al. | ..................... 604/378 |
| 5,947,945 | A | * | 9/1999 | Cree et al. | ..................... 604/368 |
| 5,947,947 | A | * | 9/1999 | Tanzer et al. | .......... 604/385.101 |
| 6,231,556 | B1 | * | 5/2001 | Osborn, III | ............... 604/385.08 |
| 6,395,956 | B1 | * | 5/2002 | Glasgow et al. | .............. 604/378 |
| 6,423,883 | B1 | * | 7/2002 | Morman et al. | ............... 604/368 |
| 6,458,113 | B2 | * | 10/2002 | Kashiwagi | ............... 604/385.16 |

(Continued)

FOREIGN PATENT DOCUMENTS
JP    10-286278 A    10/1998
(Continued)

OTHER PUBLICATIONS
PCT/JP2007/063505 International Search Report.
(Continued)

*Primary Examiner* — Tatyana Zalukaeva
*Assistant Examiner* — Susan Su
(74) *Attorney, Agent, or Firm* — Lowe, Hauptman, Ham & Berner, LLP

(57) ABSTRACT

Provided is an absorptive article having absorption elements capable of following the body of a user. This absorptive article (1) comprises a generally rectangular base absorption element (2), a top absorption element (3) disposed on one surface of the base absorption element (2) at substantially lateral center of the base absorption element (2) and along the longitudinal direction of the base absorption element (2), and a fixing part (4) for fixing the base absorption element (2) to the top absorption element (3) so that at least one end of the top absorption element (3) in the longitudinal direction thereof is made to be a free end (31). A temporary locking part (5) for restricting the movement of the top absorption element (3) is provided on the top absorption element (3) near a free end part (32) thereof at least before application of the absorptive article to the body of the user.

12 Claims, 26 Drawing Sheets

U.S. PATENT DOCUMENTS

| | | | |
|---|---|---|---|
| 6,471,682 B2 * | 10/2002 | Kashiwagi | 604/385.27 |
| 6,475,199 B1 * | 11/2002 | Gann et al. | 604/385.01 |
| 6,508,795 B1 * | 1/2003 | Samuelsson et al. | 604/378 |
| 6,595,972 B1 * | 7/2003 | Wise et al. | 604/385.01 |
| 6,761,709 B2 * | 7/2004 | Morman et al. | 604/385.101 |
| 7,090,666 B2 * | 8/2006 | Miskie | 604/385.14 |
| 7,465,297 B2 * | 12/2008 | Watanabe et al. | 604/385.101 |
| 7,549,981 B2 * | 6/2009 | Tanio et al. | 604/385.17 |
| 7,591,810 B2 * | 9/2009 | Morman et al. | 604/385.24 |
| 7,597,690 B2 * | 10/2009 | Tanio et al. | 604/389 |
| 7,621,899 B2 * | 11/2009 | Fujikawa et al. | 604/385.101 |
| 7,629,501 B2 * | 12/2009 | Labit et al. | 604/372 |
| 7,648,490 B2 * | 1/2010 | Kuroda et al. | 604/385.01 |
| 7,842,019 B2 * | 11/2010 | Sugiyama et al. | 604/385.01 |
| 7,847,145 B2 * | 12/2010 | Kurita et al. | 604/378 |
| 2002/0143309 A1 * | 10/2002 | Glasgow et al. | 604/378 |
| 2002/0193766 A1 | 12/2002 | Gell et al. | |
| 2006/0282059 A1 * | 12/2006 | Fujikawa et al. | 604/385.17 |
| 2008/0172019 A1 * | 7/2008 | Chien | 604/385.04 |

FOREIGN PATENT DOCUMENTS

| | | | |
|---|---|---|---|
| JP | 11-104169 A | | 4/1999 |
| JP | 2000-152957 A | | 6/2000 |
| JP | 2001245921 A | | 9/2001 |
| JP | 2002-159534 A | | 6/2002 |
| JP | 2002159534 A | * | 6/2002 |
| JP | 2008023248 A | | 2/2008 |

OTHER PUBLICATIONS

Office Action issued to the U.S. Appl. No. 12/307,033 mailed Oct. 12, 2011.

* cited by examiner

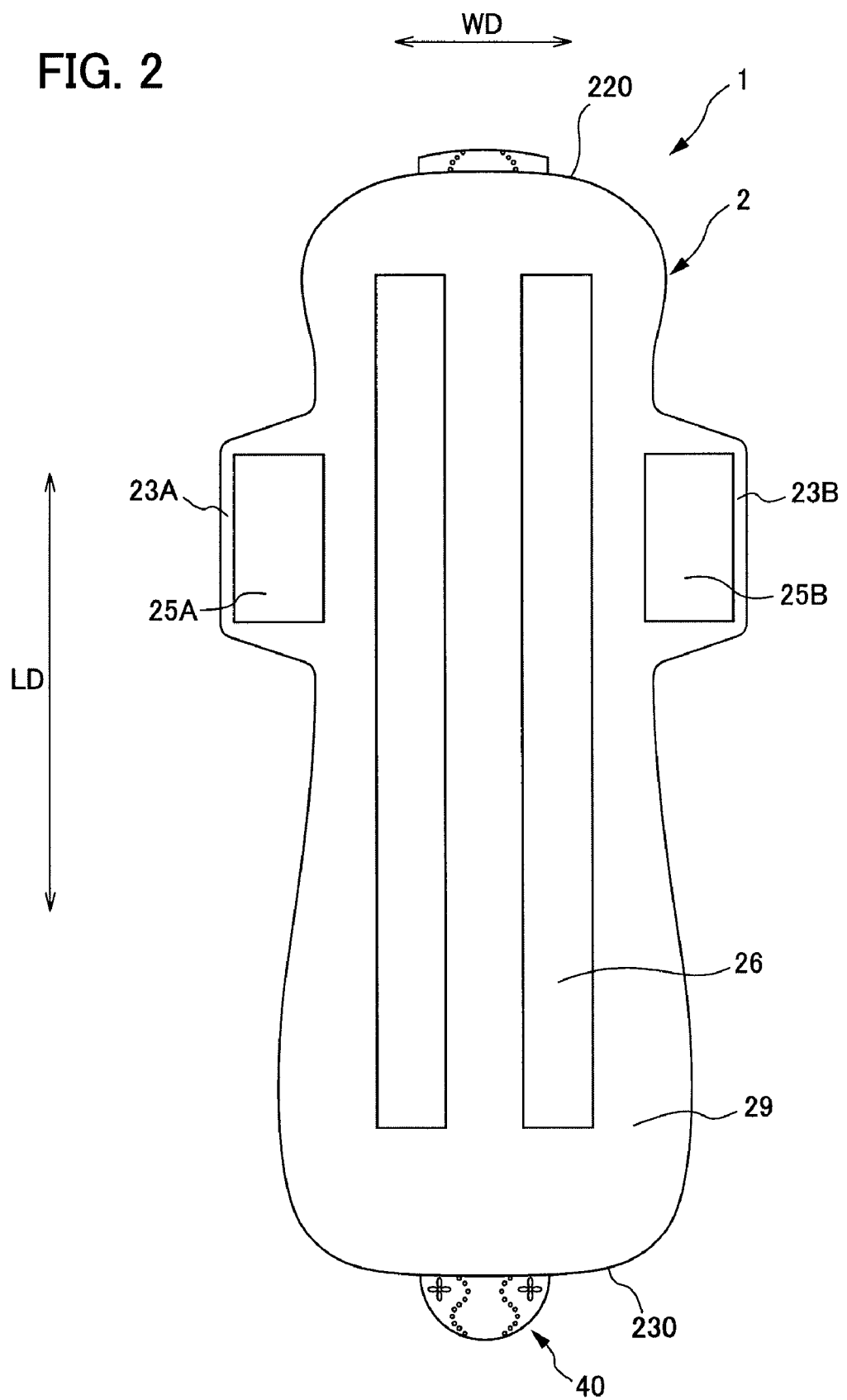

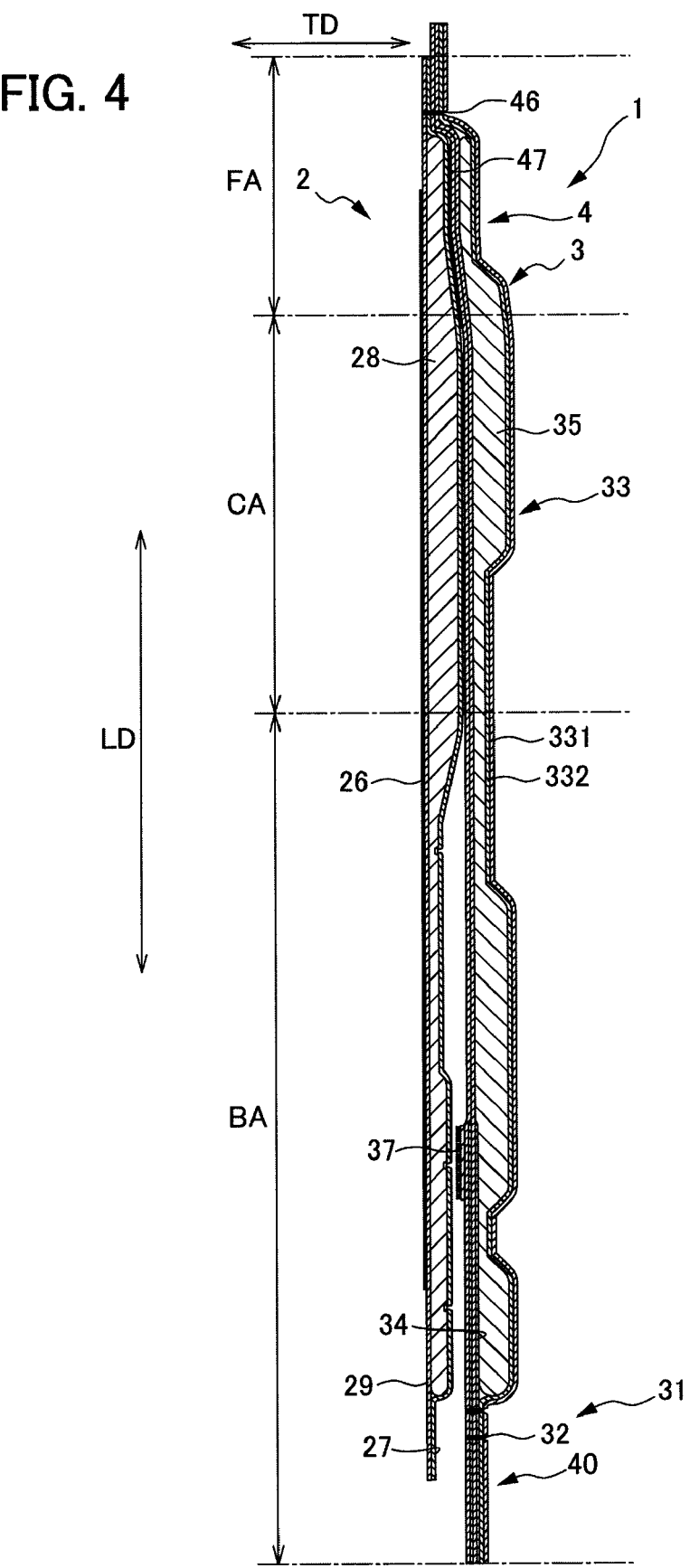

ABSORPTIVE ARTICLE

RELATED APPLICATIONS

The present application is based on, International Application Number PCT/JP2007/063505, filed Jul. 5, 2007 which claims priority from, Japan Application Number 2006-186142, filed Jul. 5, 2006, the disclosures of which are hereby incorporated by reference herein in their entirety.

TECHNICAL FIELD

The present invention relates to an absorbent article.

BACKGROUND ART

Conventionally, as an absorbent article for absorbing a predetermined liquid such as menstrual blood, an absorbent article that is entirely formed in a sheet-like shape, including an absorbent layer for absorbing the predetermined liquid, a liquid permeable top sheet for covering a skin contacting surface of the absorbent layer, and a liquid impermeable back surface sheet for covering a clothing side surface of the absorbent layer, can be exemplified. Such an absorbent article, which is substantially sheet-shaped, is used in contact with an excretory part, and directly absorbs the liquid such as menstrual blood discharged from the excretory part. Various improvements have been made thereto in order to prevent menstrual blood and the like, which runs along a predetermined groove of a wearer's body, from contacting clothing and the like.

For example, a means for preventing leakage of menstrual blood includes wings projecting in a width direction, provided on both sides of an absorbent article, for fixing the absorbent article by being folded back toward underwear, and for raising an absorbent core in a vicinity of an excretory part of menstrual blood toward the excretory part in order to make the absorbent core adhere to the excretory part in order to absorb menstrual blood. However, such absorbent articles may not appropriately follow movement of a wearer's body and change in body surface shape due to movement.

In contrast, an absorbent article is proposed including a lower absorbent core fixed to an absorbent article main body and an upper absorbent core independent therefrom, in which an elastic, stretchable intermediate sheet disposed in a longitudinal direction between the upper absorbent core and the lower absorbent core pushes up the upper absorbent core and makes the upper absorbent core adhere to a wearer's body, in order to improve followability with respect to an excretory part (for example, see Japanese Unexamined Patent Application Publication No. 2000-152957).

[Patent Document 1] Japanese Unexamined Patent Application Publication No. 2000-152957

DISCLOSURE OF THE INVENTION

Problems to be Solved by the Invention

However, in the case of an absorbent article according to Patent Document 1, an upper absorbent core is entirely fixed to a lower absorbent core of a sanitary napkin in the longitudinal direction, and at both ends of the lower absorbent core in the width direction. Therefore, the uppermost side makes a wide flat plane in the width direction when it is attached. Since this makes a predetermined space between the upper absorbent core and the groove of a wearer's body, a tight fit without any space between the upper absorbent core and an excretion area inside of the groove of the wearer's body is not possible, causing leakage of menstrual blood.

In addition, the upper absorbent core is capable of following the body by deforming the upper absorbent core if movement of the wearer's body in the lateral direction is slight; however, it is incapable of following large movements of the wearer's body or underwear in the width direction that are greatly dislocating, or movement of the wearer's body or underwear in the longitudinal direction.

Moreover, since the upper absorbent core is entirely fixed to the lower absorbent core in the longitudinal direction, a user should attach the sanitary napkin to the underwear at a position hidden from the user, resulting in the upper absorbent core not always being attached successfully in a tight fit to the groove of the wearer's body. If the upper absorbent core cannot be attached so as to tightly fit to the groove of the wearer's body, a predetermined space may generate between the upper absorbent core and the excretion area, causing leakage.

The present invention is devised in view of the aforementioned problems, and aims to provide an absorbent article having an absorbent core capable of following the wearer's body.

Means for Solving the Problems

A first aspect of the invention is an absorbent article, which includes: a substantially rectangular first absorbent core (for example, a base absorbent core 2 according to a following first embodiment); a second absorbent core, which is provided on a skin contacting side of the first absorbent core along a longitudinal direction of the first absorbent core (for example, a top absorbent core 3 according to the following first embodiment); a fixing portion, which fixes the first absorbent core and the second absorbent core so that at least one end of the second absorbent core in the longitudinal direction serves as a free end; and temporary fixing portions, which are formed between the fixing portion and the free end.

A second aspect of the invention is the absorbent article of the first aspect, wherein the absorbent article includes a front edge, which is an outer edge in the longitudinal direction and close to a first position contacting with an excretion area in a state attached to an attaching target, and a rear edge, which is far from the first position; wherein the fixing portion is formed between the first position and the front edge.

A third aspect of the invention is the absorbent article of the first or the second aspect, wherein the temporary fixing portions are formed on the free end side of the second absorbent core.

A fourth aspect of the invention is the absorbent article of any of the first through the third aspect, which further includes a handle part, which is formed at the free end of the second absorbent core.

A fifth aspect of the invention is the absorbent article of any of the first through the fourth aspect, wherein the second absorbent core includes a locking portion, which is provided on the free end side; and the locking portion also serves as the temporary fixing portions.

A sixth aspect of the invention is the absorbent article of fifth aspect, wherein in an attached state, the locking portion locks the free end further on an outer edge side in the longitudinal direction of the first absorbent core than a position when the first absorbent core and the second absorbent core are formed into an approximate flat plane.

A seventh aspect of the invention is the absorbent article of the fifth aspect, wherein when the absorbent article is provided between the attaching target and garment which is provided so as to cover the attaching target, and the locking portion is locked on the inside of the garment, or locked on the outside of the garment by folding back the second absorbent core.

An eighth aspect of the invention is the absorbent article of any of the first through the seventh aspect, wherein the second absorbent core has a length in a width direction orthogonal to the longitudinal direction in a range from 40% to 90% of length in the width direction of the first absorbent core.

A ninth aspect of the invention is the absorbent article of the eighth aspect, wherein the second absorbent core has leakage-preventing wall members provided so as to extend in the longitudinal direction in both side portions which are both ends in the width direction.

A tenth aspect of the invention is an absorbent article, which is a substantially rectangular shape and attached to an attaching target having an excretion area, and includes: a substantially rectangular first absorbent core; a second absorbent core, which is provided on a skin contacting side of the first absorbent core along a longitudinal direction of the first absorbent core; and a fixing portion, which fixes the first absorbent core and the second absorbent core so that one edge of the second absorbent core serves as a free end; wherein the fixing portion is formed on a rear edge side far from a first position making contact with the excretion area in the longitudinal direction while the absorbent article is attached to the attaching target; and the free end is provided on a front edge side close to the first position in the longitudinal direction.

An eleventh aspect of the invention is an absorbent article, which is attached to an attaching target having an excretion area, and includes: a substantially rectangular first absorbent core; a second absorbent core, which is provided on a skin contacting side of the first absorbent core along a longitudinal direction of the first absorbent core; and a fixing portion, which fixes the first absorbent core and the second absorbent core; wherein the fixing portion is formed at a position separated from respective ends of the second absorbent core in the longitudinal direction; and the second absorbent core includes a first free end, which is provided on a front edge side close to a first position making contact with the excretion area in the longitudinal direction while the absorbent article is attached to the attaching target, and a second free end, which is provided on a rear edge side far from the first position in the longitudinal direction.

Effects of the Invention

According to the present invention, it is possible to provide an absorbent article having an absorbent core capable of following the wearer's body.

BRIEF DESCRIPTION OF THE DRAWINGS

FIG. 2 is a back view of the absorbent article according to the first embodiment of the present invention.

FIG. 4 is a longitudinal cross-sectional view of the absorbent article of FIG. 1 cut along the line Y-Y, according to the first embodiment of the present invention.

PREFERRED MODE FOR CARRYING OUT THE INVENTION

Figure 1:
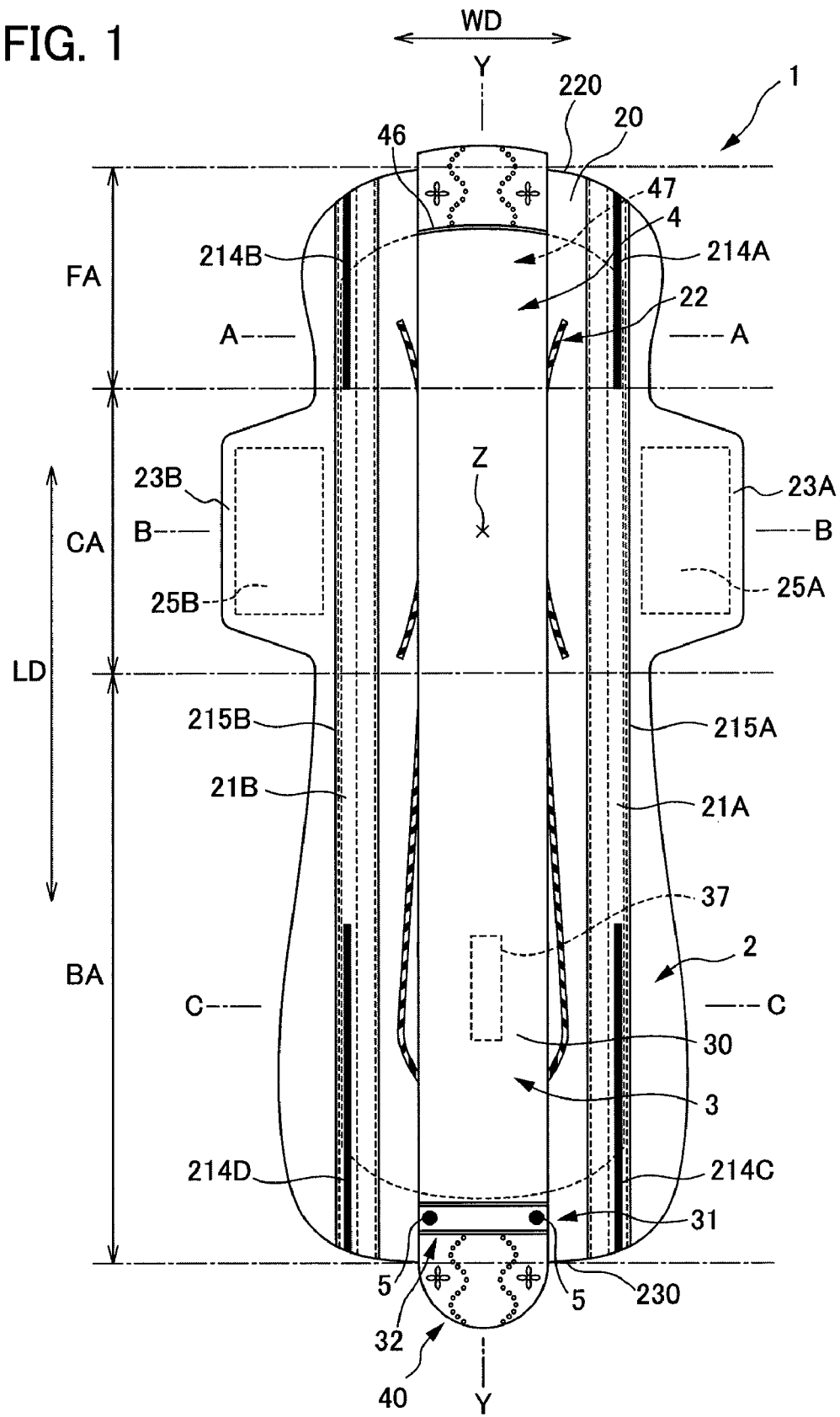
FIG. 1 is a plan view of an absorbent article according to a first embodiment of the present invention.
Figure 3A:
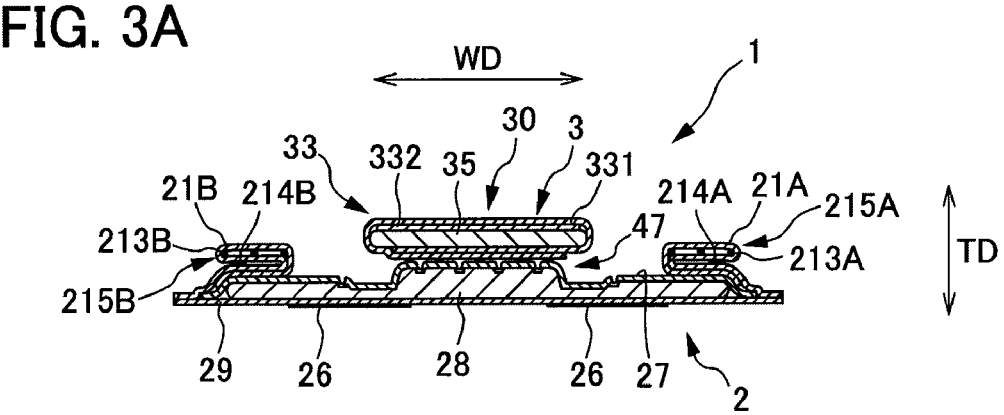
FIG. 3A is a lateral cross-sectional view of the absorbent article of FIG. 1 according to the first embodiment of the present invention.
Figure 3B:
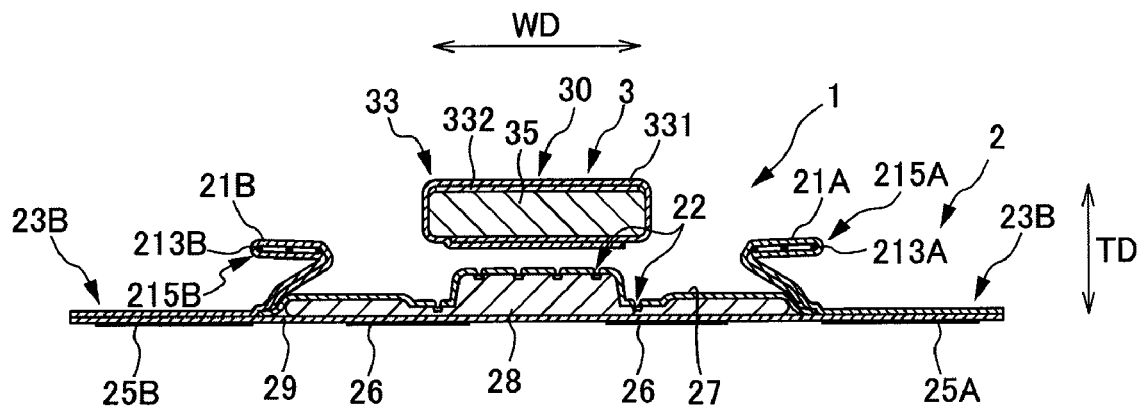
FIG. 3B is a lateral cross-sectional view of the absorbent article of FIG. 1 according to the first embodiment of the present invention.
Figure 3C:
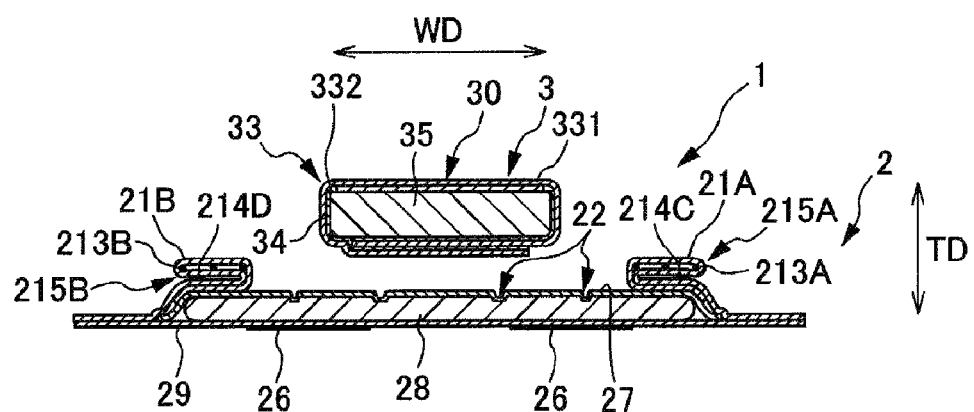
FIG. 3C is a lateral cross-sectional view of the absorbent article of FIG. 1 according to the first embodiment of the present invention.
Figure 5:
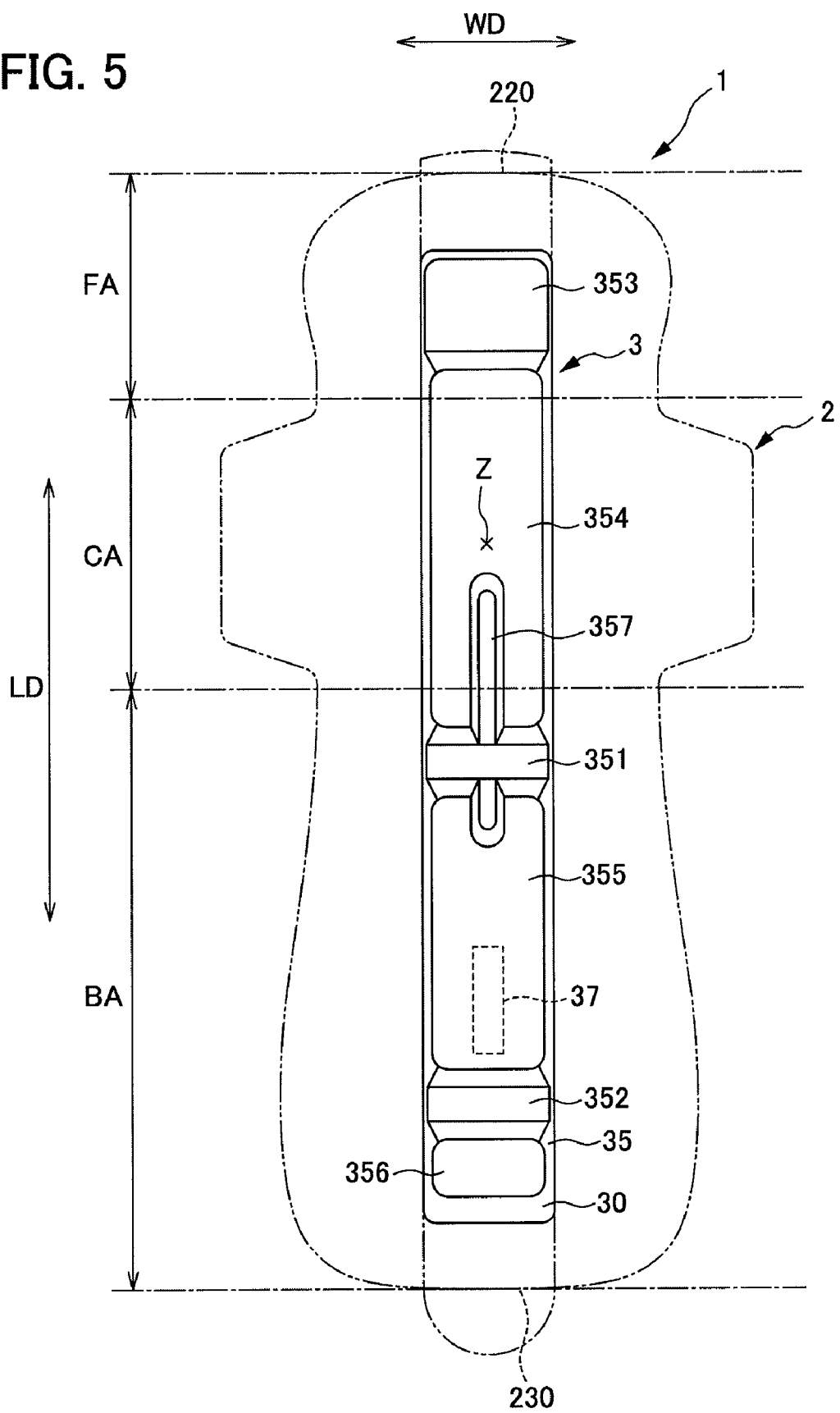
FIG. 5 is a drawing showing an absorbent core placed on a top absorbent core according to the first embodiment of the present invention.
Figure 6:
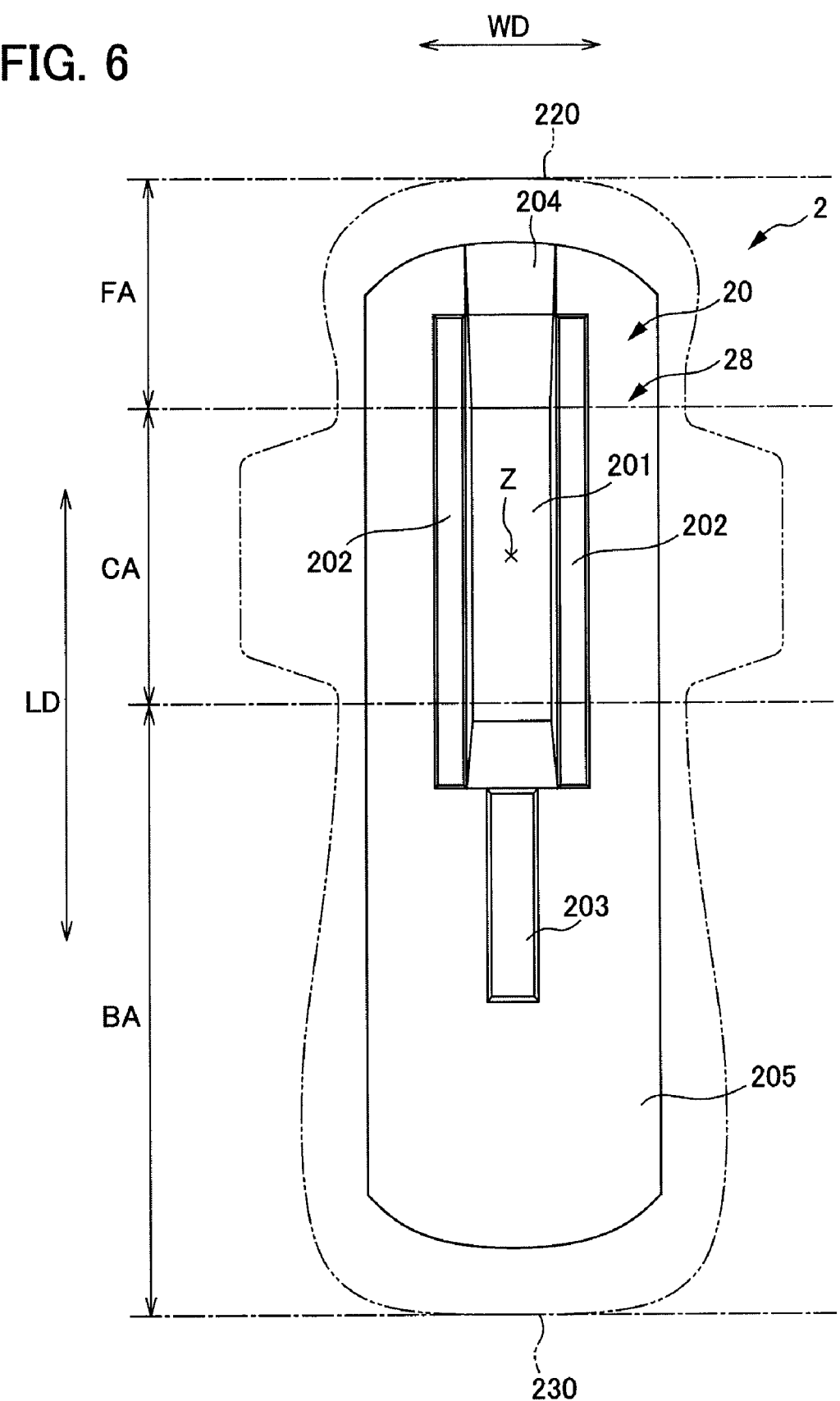
FIG. 6 is a drawing showing an absorbent core placed on a base absorbent core according to the first embodiment of the present invention.
Figure 7:
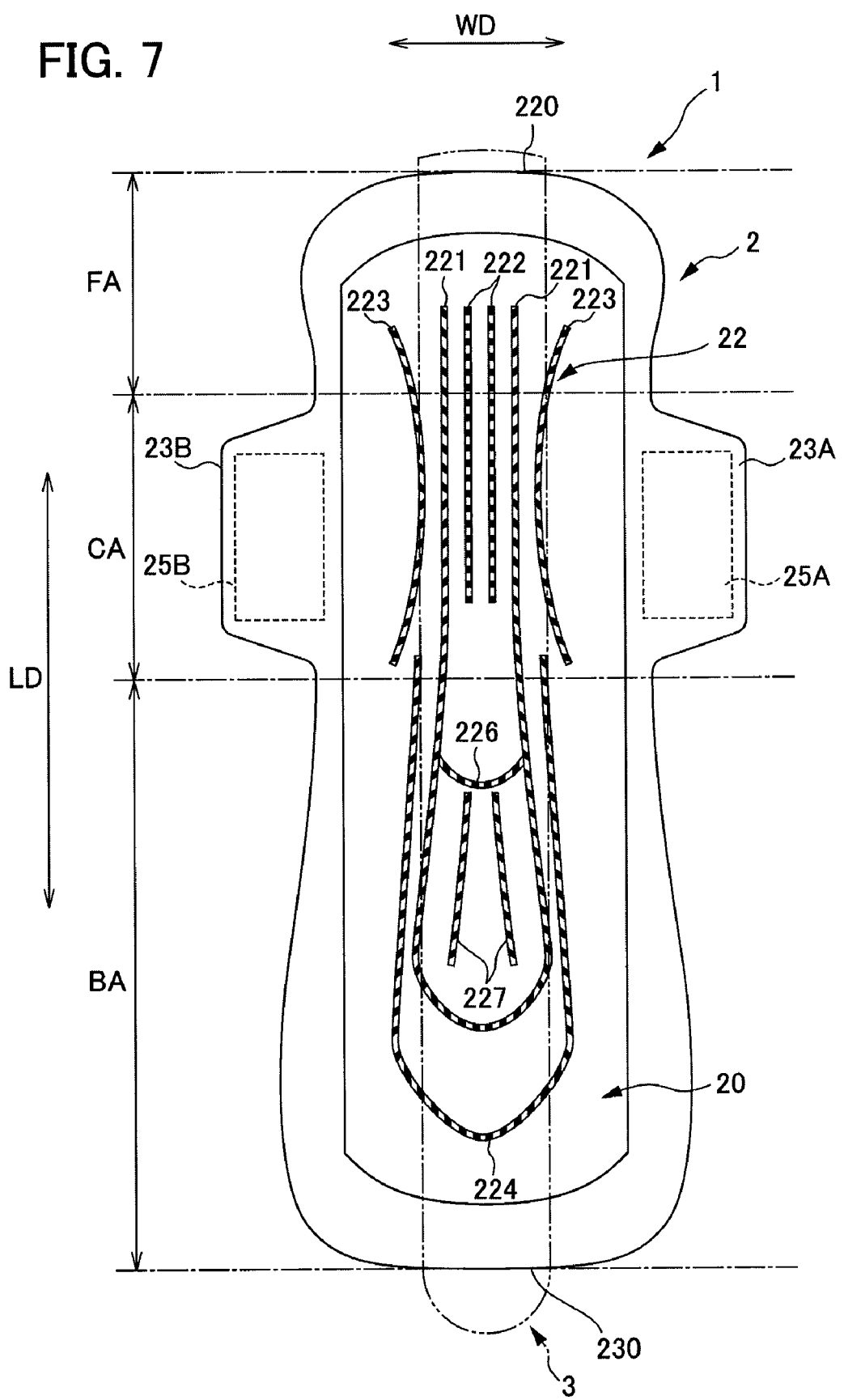
FIG. 7 is a drawing showing compressed grooves of the base absorbent core according to the first embodiment of the present invention.
Figure 8:
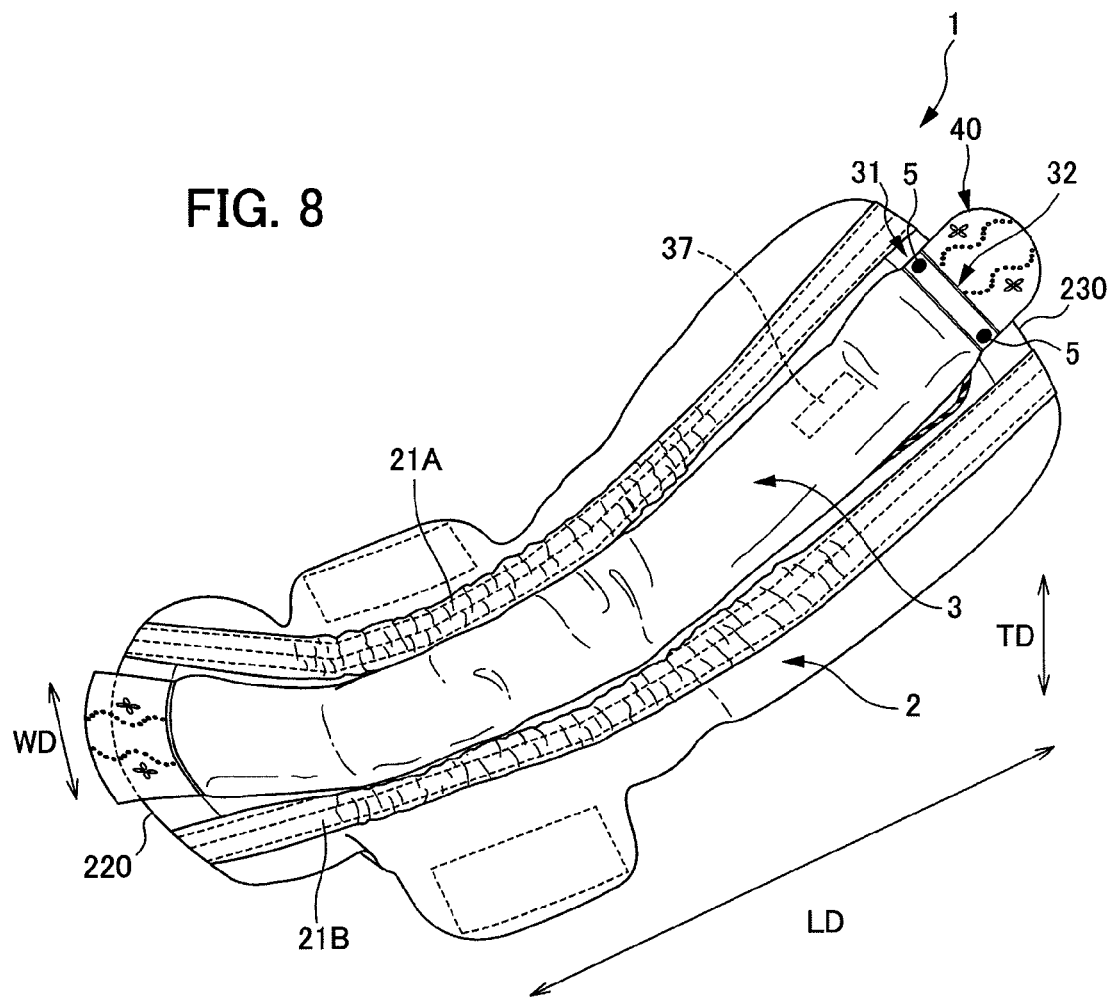
FIG. 8 is a perspective view of the absorbent article in use according to the first embodiment of the present invention.
Figure 9:
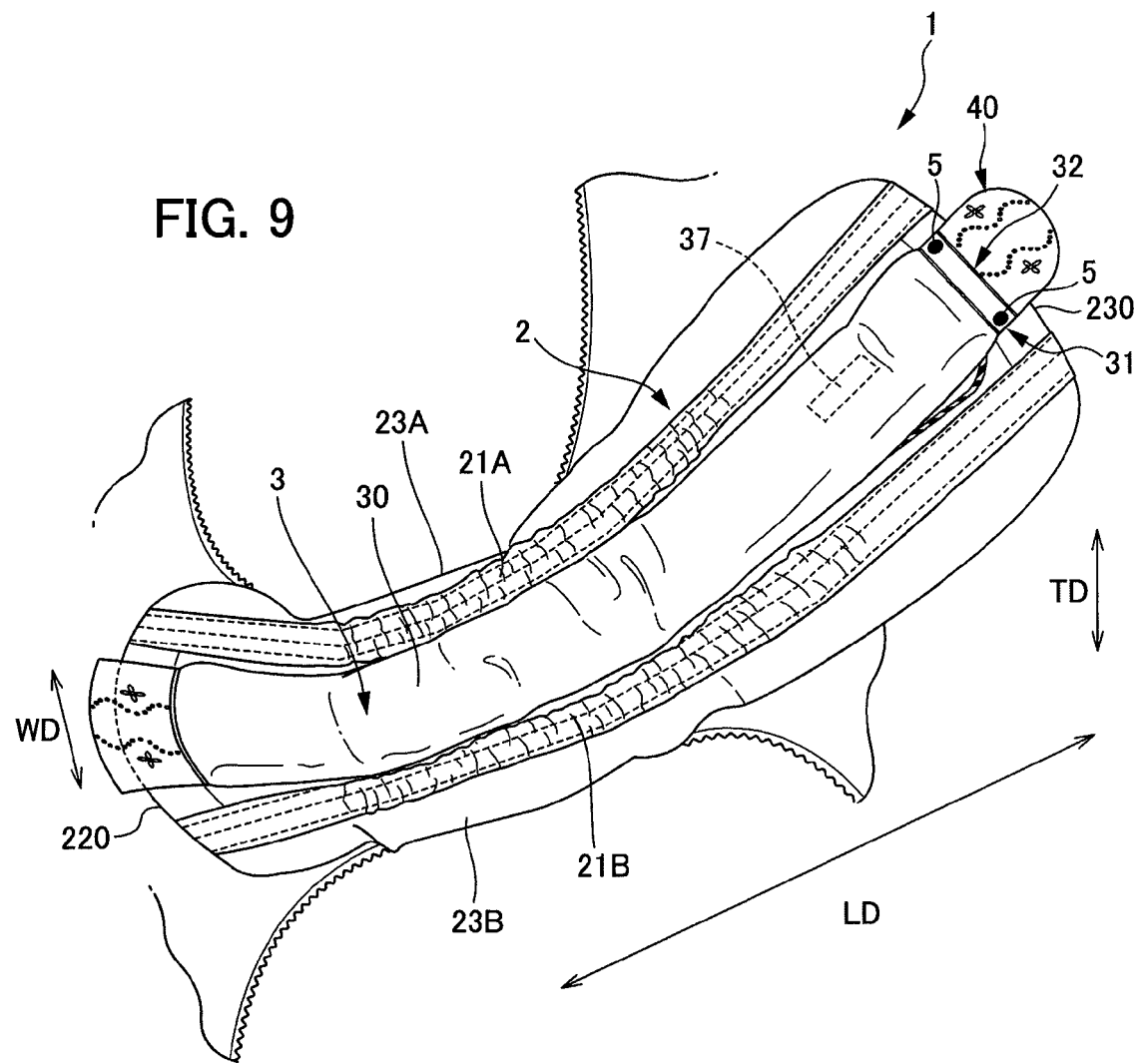
FIG. 9 is a perspective view of the absorbent article in use according to the first embodiment of the present invention.
Figure 10:
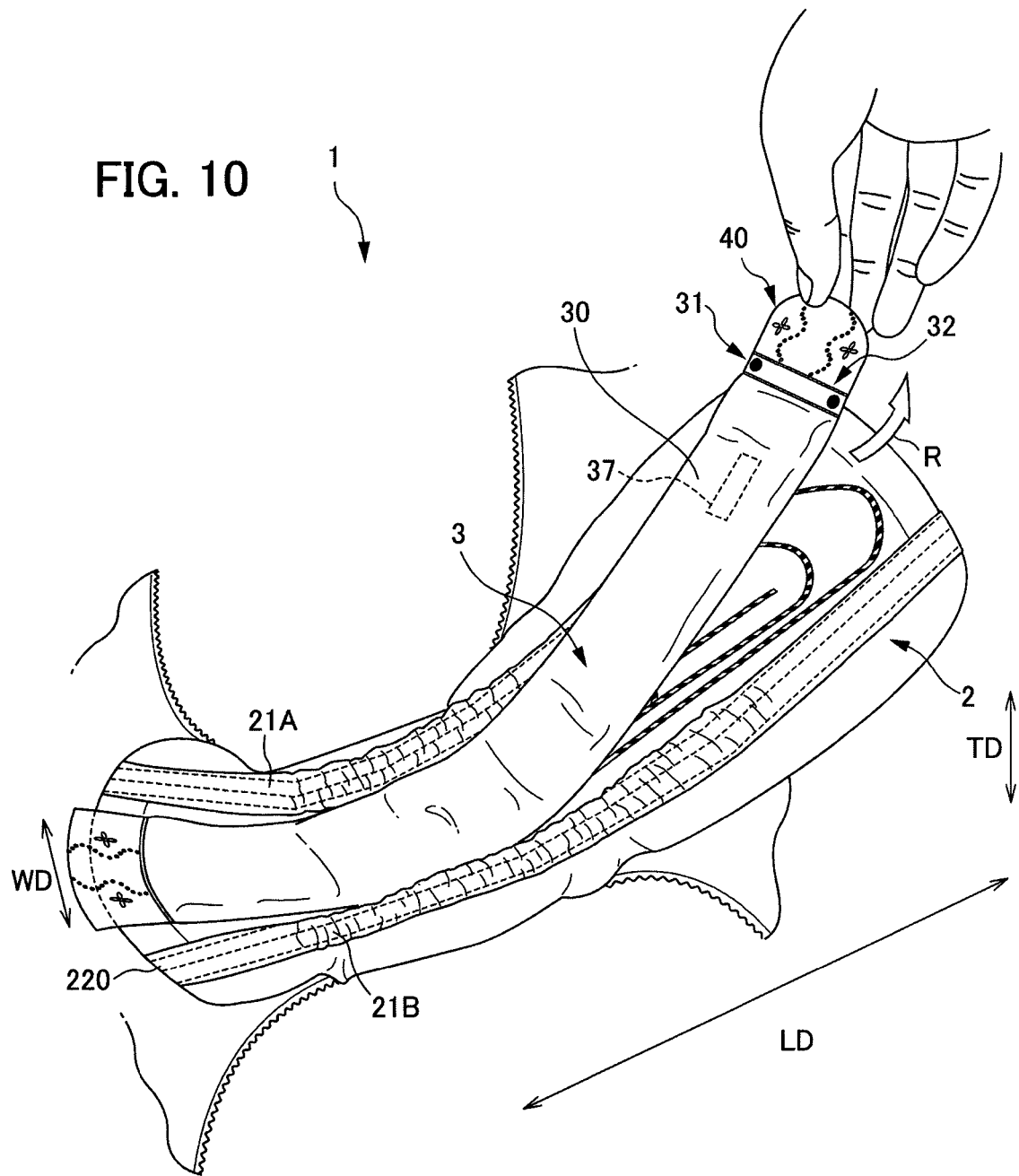
FIG. 10 is a perspective view of the absorbent article in use according to the first embodiment of the present invention.
Figure 11:
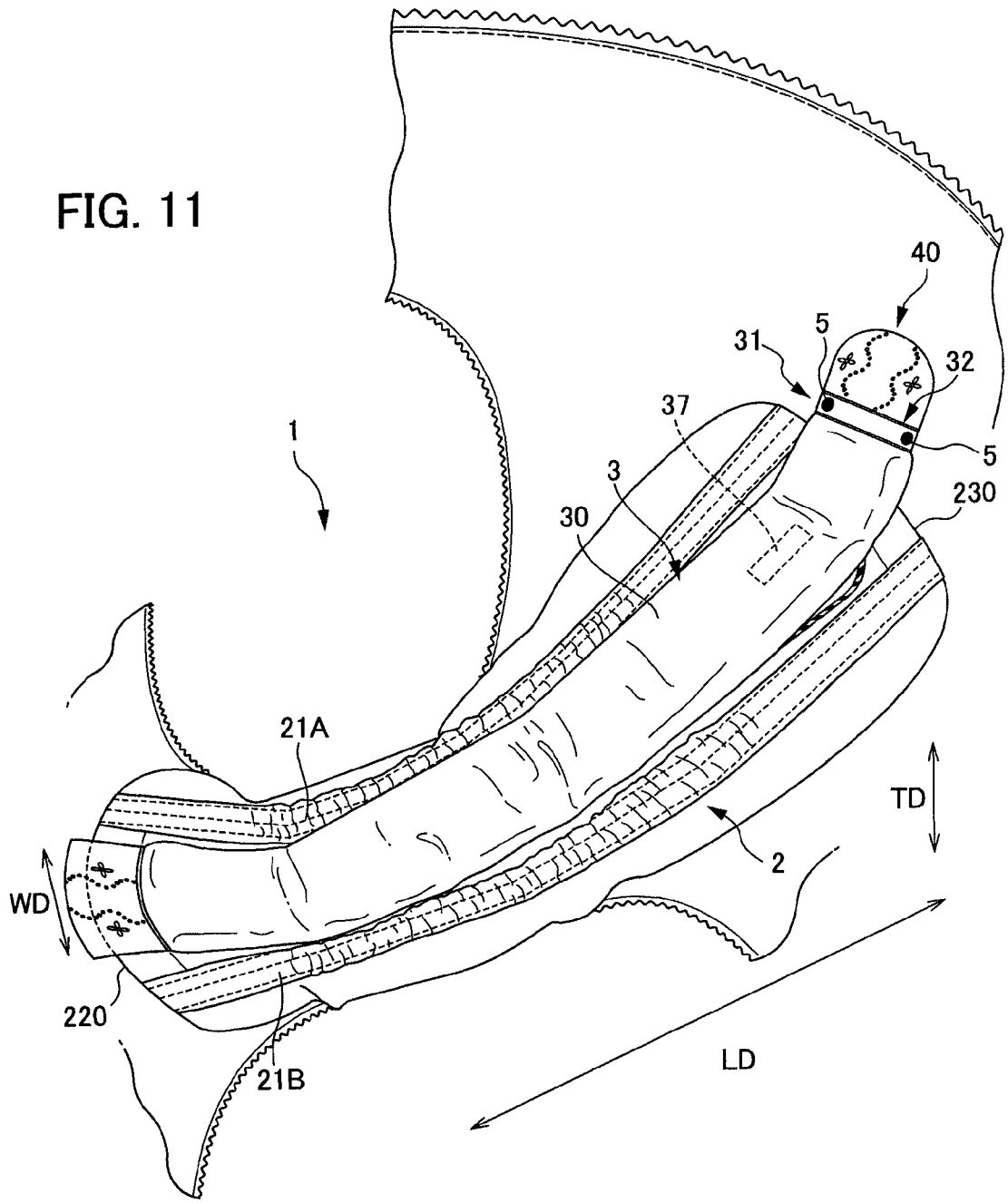
FIG. 11 is perspective view of the absorbent article in use according to the first embodiment of the present invention.

FIG. 1 is a plan view of an absorbent article according to a first embodiment of the present invention. FIG. 2 is a back view of the absorbent article according to the first embodiment of the present invention. FIG. 3A is a lateral cross-sectional view of the absorbent article of FIG. 1 cut along the line A-A, according to the first embodiment of the present invention. FIG. 3B is a lateral cross-sectional view of the absorbent article of FIG. 1 cut along the line B-B, according to the first embodiment of the present invention. FIG. 3C is a lateral cross-sectional view of the absorbent article of FIG. 1 cut along the line C-C, according to the first embodiment of the present invention. FIG. 4 is a longitudinal cross-sectional view of the absorbent article of FIG. 1 cut along the line Y-Y, according to the first embodiment of the present invention. FIG. 5 is a drawing showing an absorbent core placed on a top absorbent core according to the first embodiment of the present invention. FIG. 6 is a drawing showing an absorbent core placed on a base absorbent core according to the first embodiment of the present invention. FIG. 7 is a drawing showing compressed grooves of the base absorbent core according to the first embodiment of the present invention. FIG. 8 is a perspective view of the absorbent article in use according to the first embodiment of the present invention. FIG. 9 is a perspective view of the absorbent article in use according to the first embodiment of the present invention. FIG. 10 is a perspective view of the absorbent article in use according to the first embodiment of the present invention. FIG. 11 is a perspective view of the absorbent article in use according to the first embodiment of the present invention.

Figure 12:
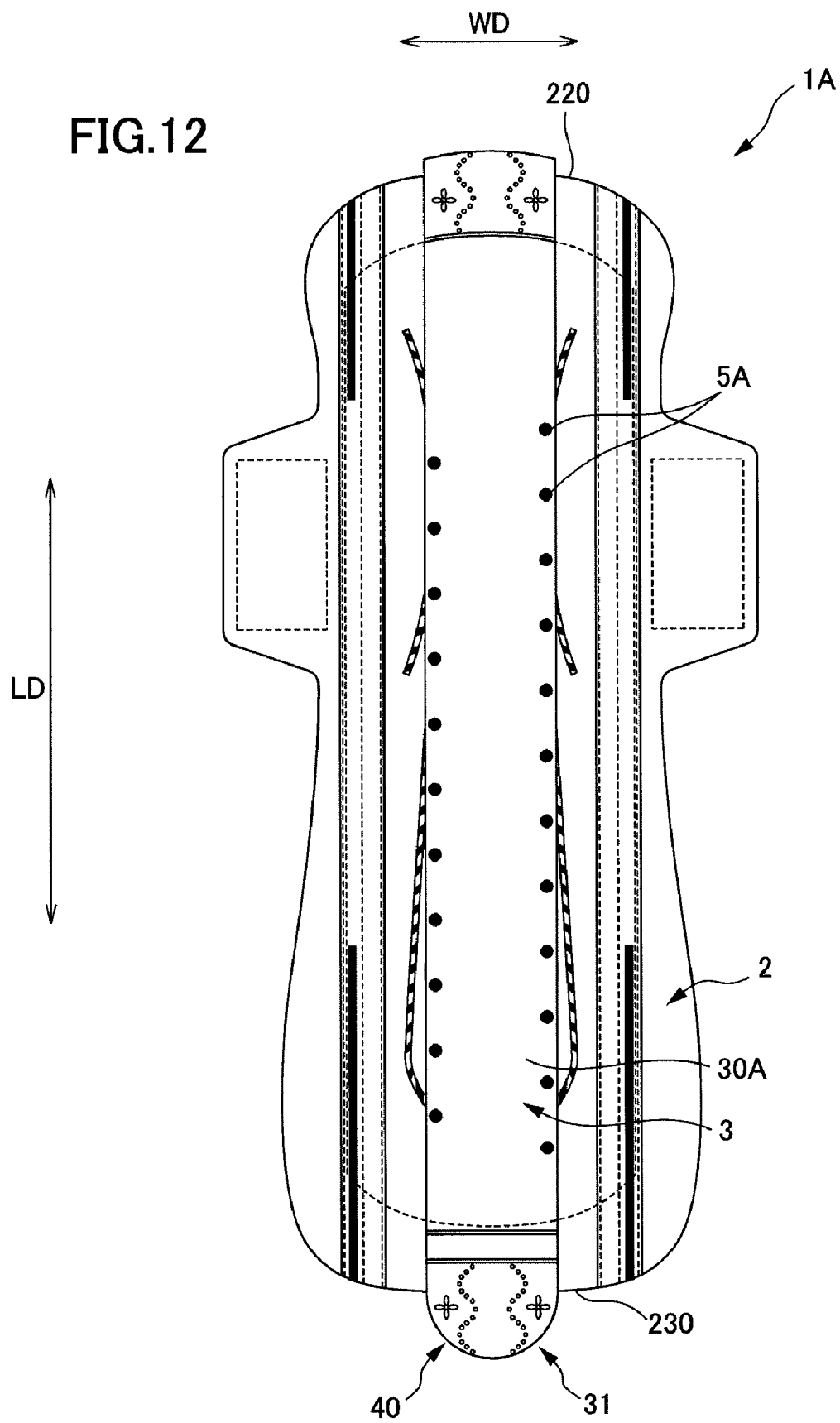
FIG. 12 is a plan view of an absorbent article according to a second embodiment of the present invention.
Figure 13:
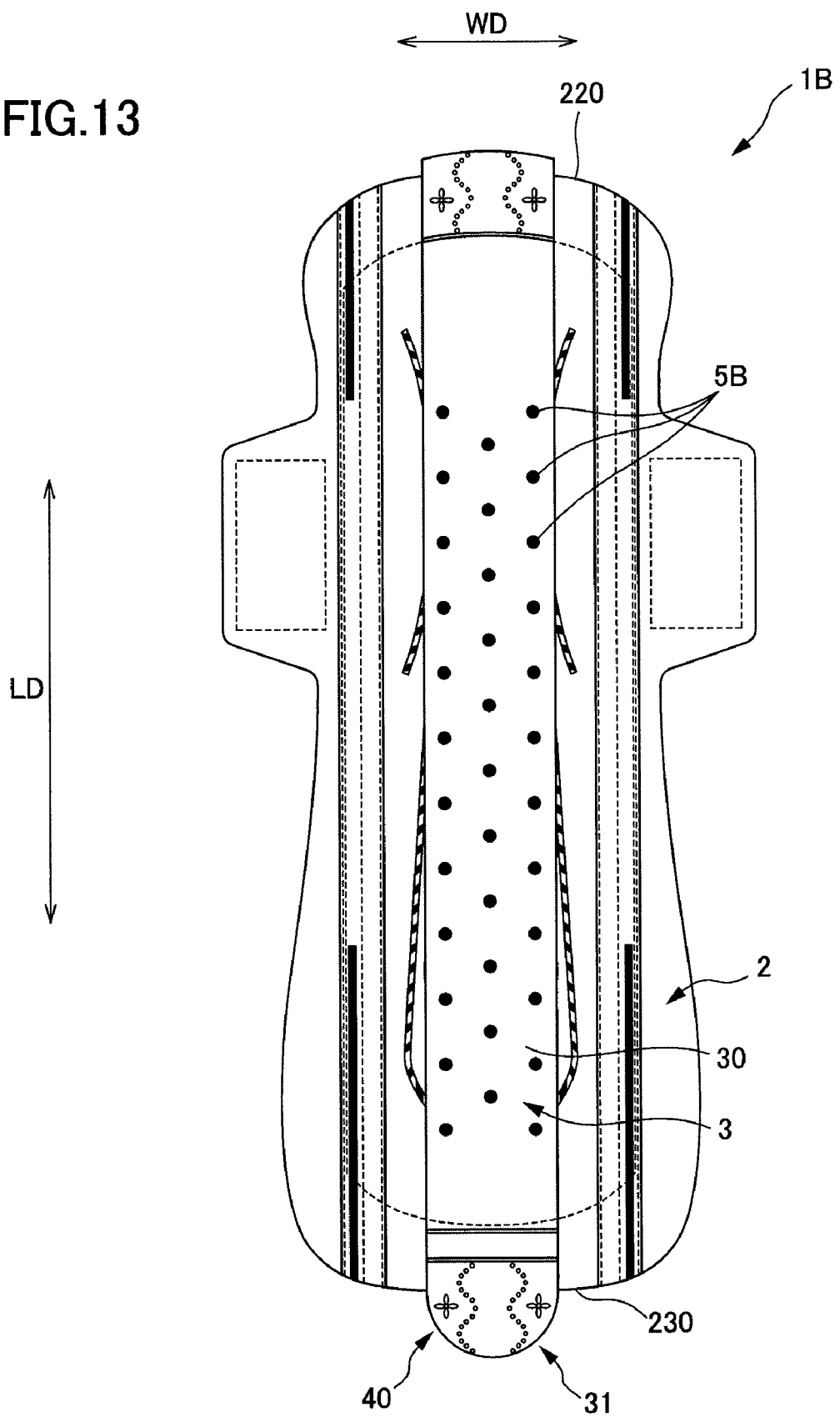
FIG. 13 is a plan view of an absorbent article according to a third embodiment of the present invention.
Figure 14A:
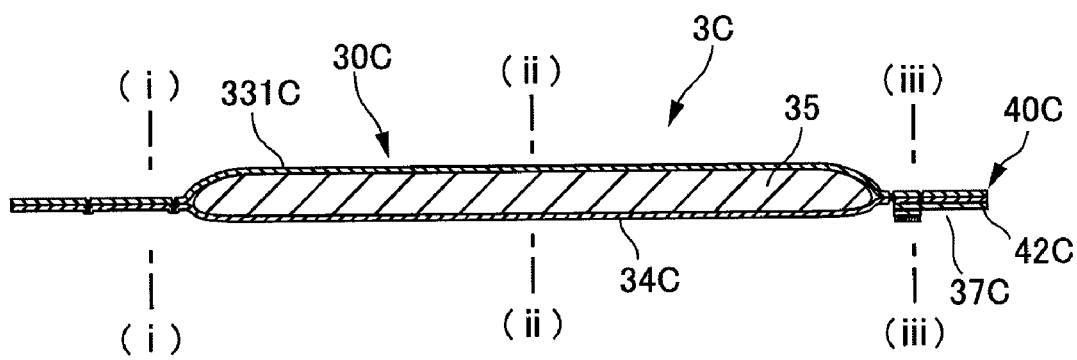
FIG. 14A is a longitudinal cross-sectional view of a top absorbent core according to a fourth embodiment of the present invention.
Figure 14B:
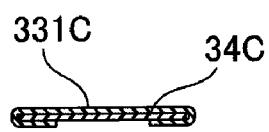
FIG. 14B is a lateral cross-sectional view of the top absorbent core according to the fourth embodiment of the present invention.
Figure 14C:
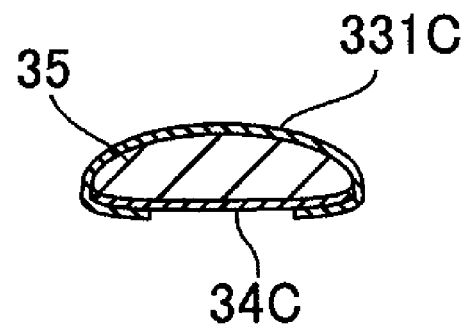
FIG. 14C is a lateral cross-sectional view of the top absorbent core according to the fourth embodiment of the present invention.
Figure 14D:
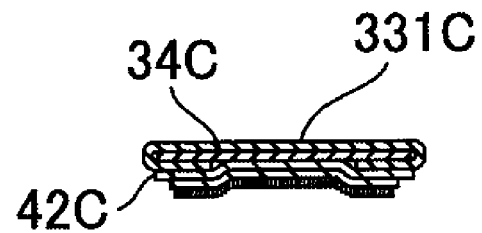
FIG. 14D is a lateral cross-sectional view of the top absorbent core according to the fourth embodiment of the present invention.
Figure 15:
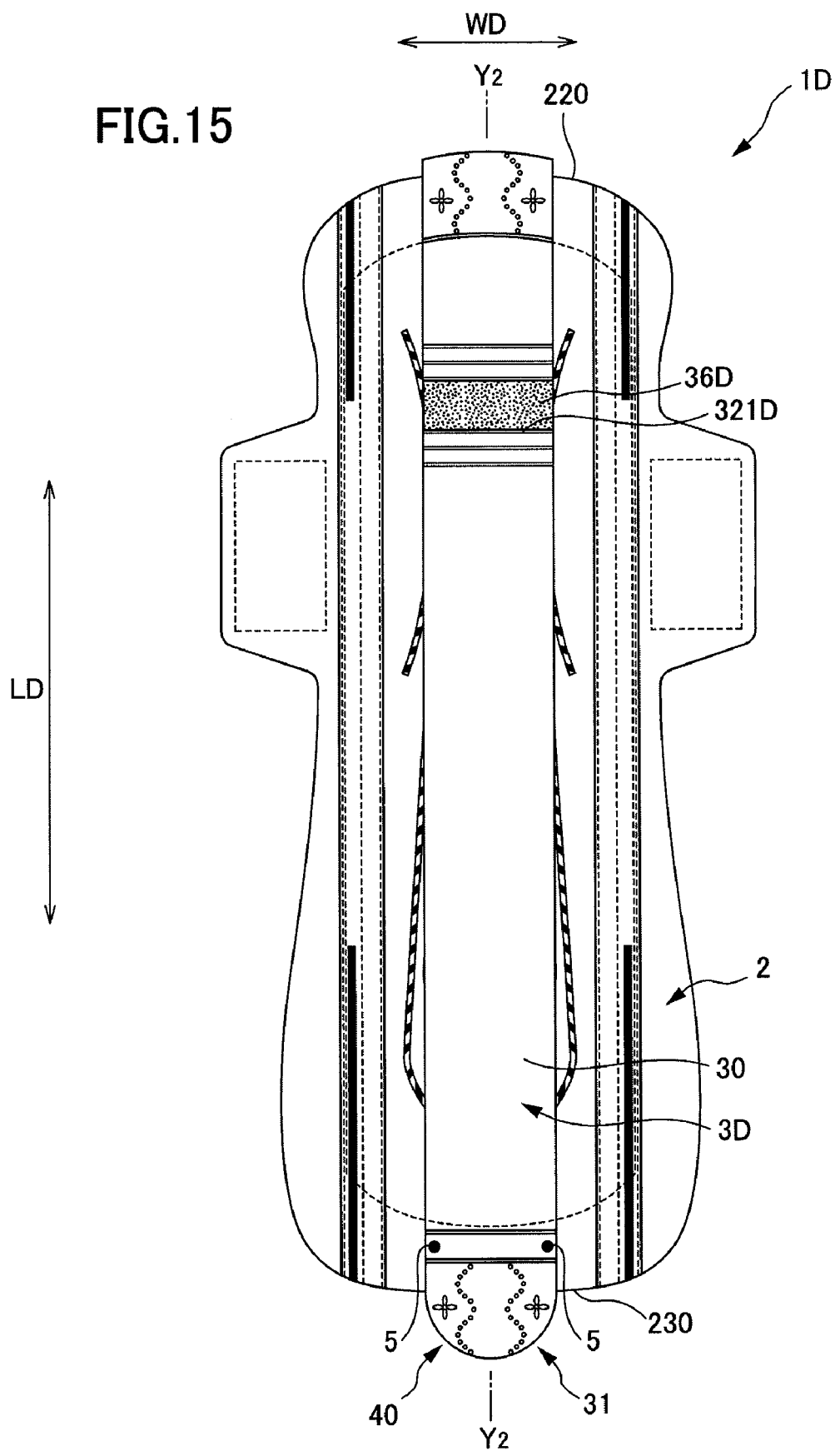
FIG. 15 is a plan view of an absorbent article according to a fifth embodiment of the present invention.
Figure 16:
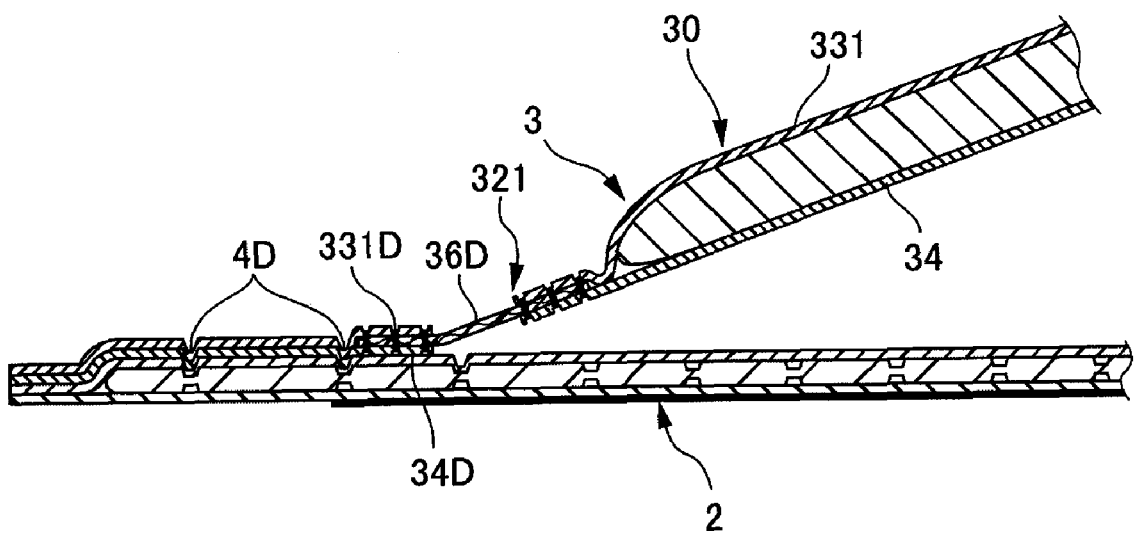
FIG. 16 is a magnified longitudinal cross-sectional view near a fixing portion of the absorbent article according to the fifth embodiment of the present invention.
Figure 17:
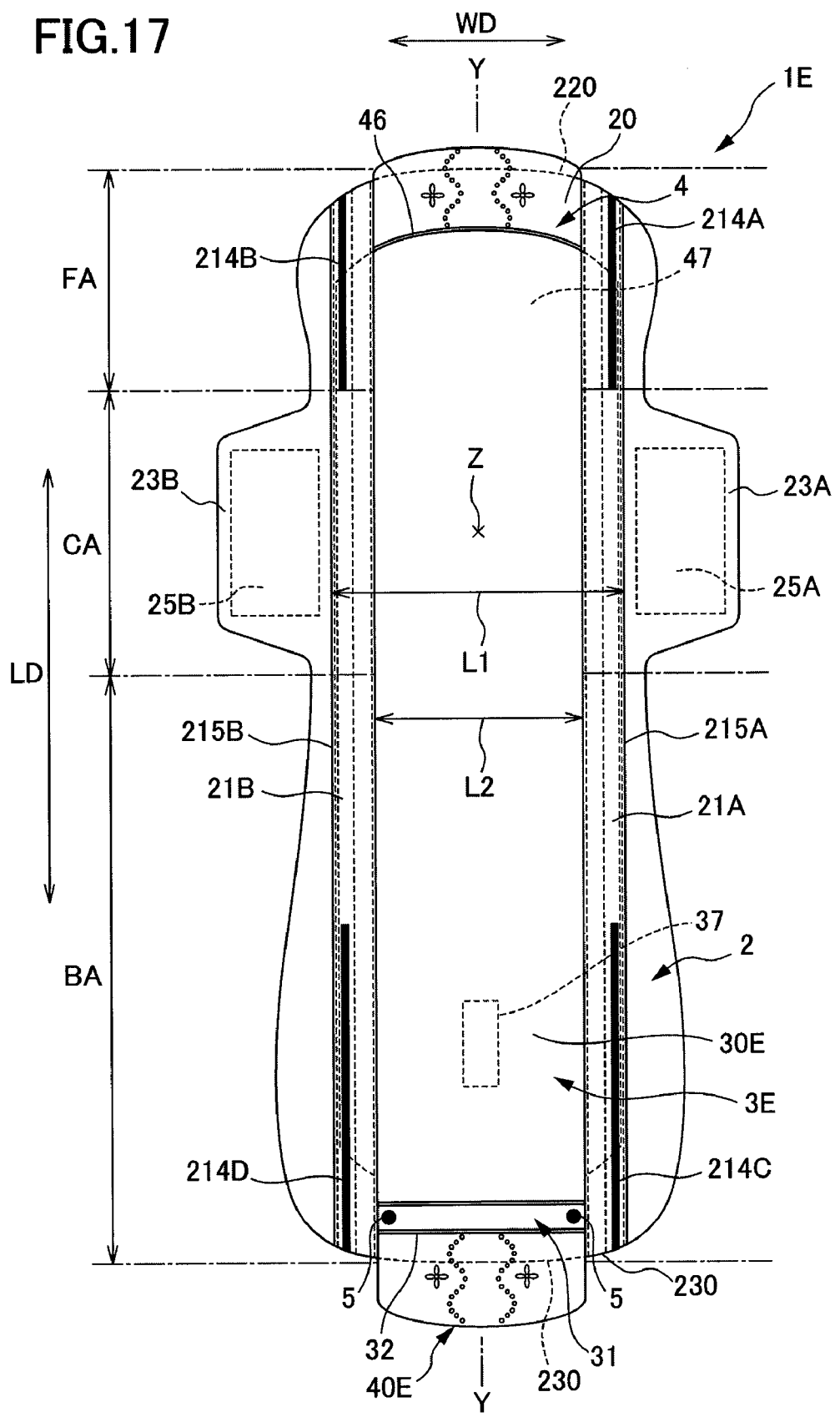
FIG. 17 is a plan view of an absorbent article according to a sixth embodiment of the present invention.
Figure 18A:
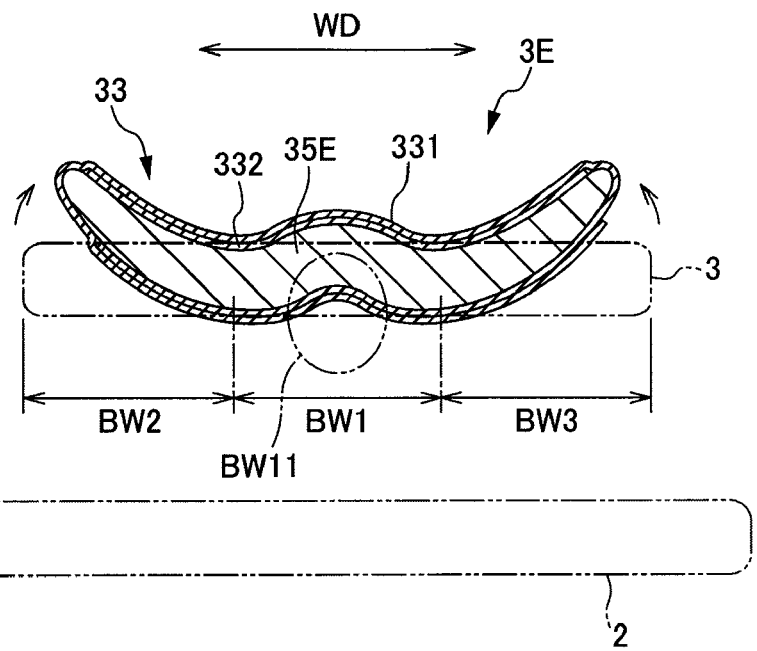
FIG. 18A is a lateral cross-sectional view of a top absorbent core of the absorbent article according to the sixth embodiment of the present invention.
Figure 18B:
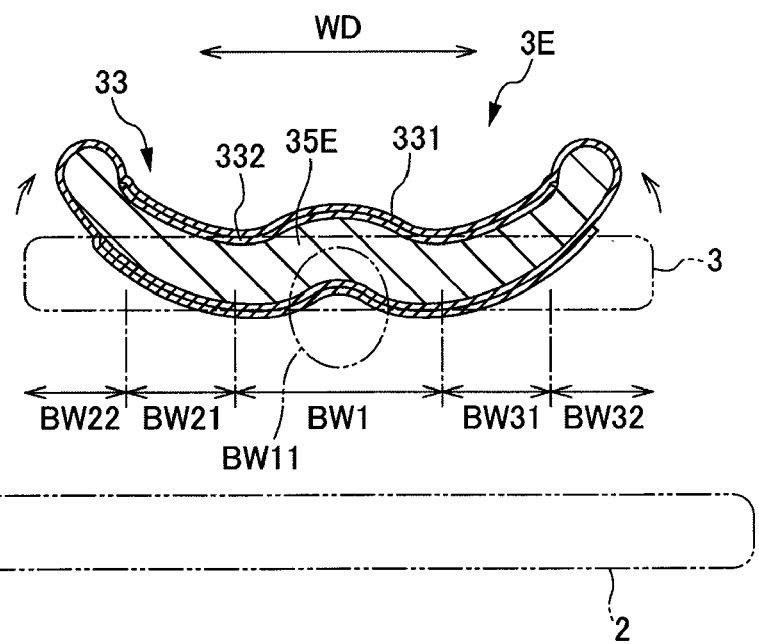
FIG. 18B is a lateral cross-sectional view of the top absorbent core of the absorbent article according to the sixth embodiment of the present invention.
Figure 19A:
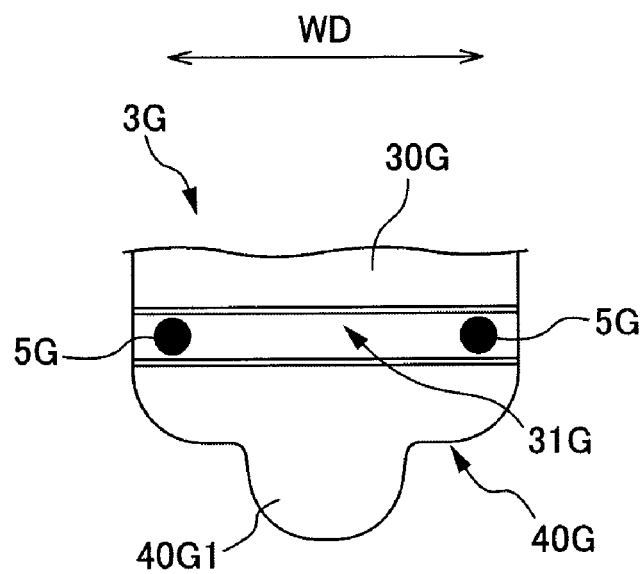
FIG. 19A is a plan view of an absorbent article according to a seventh embodiment of the present invention.
Figure 19B:
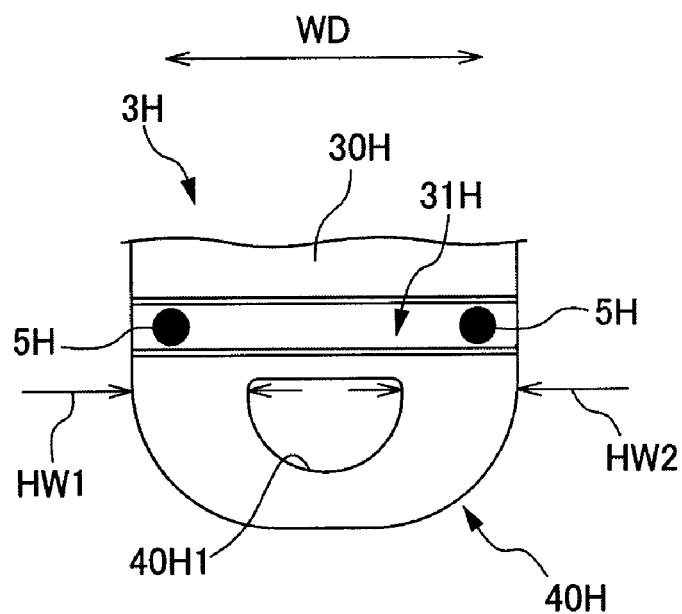
FIG. 19B is a plan view of the absorbent article according to the seventh embodiment of the present invention.
Figure 20A:
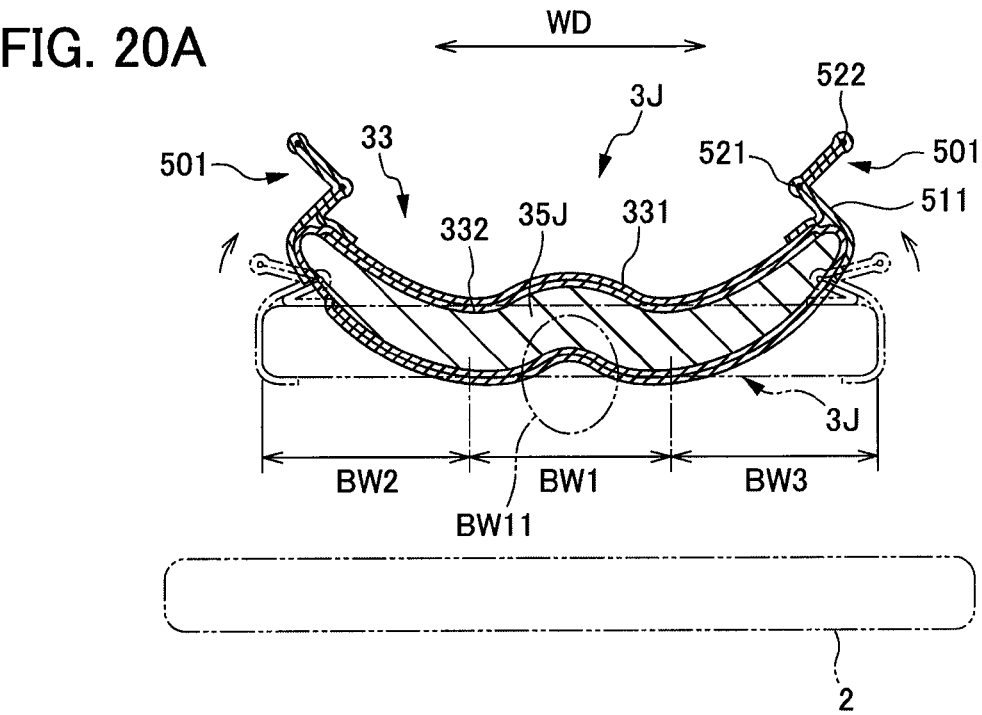
FIG. 20A is a magnified plan view near a handle part of an absorbent article according to an eighth embodiment of the present invention.
Figure 20B:
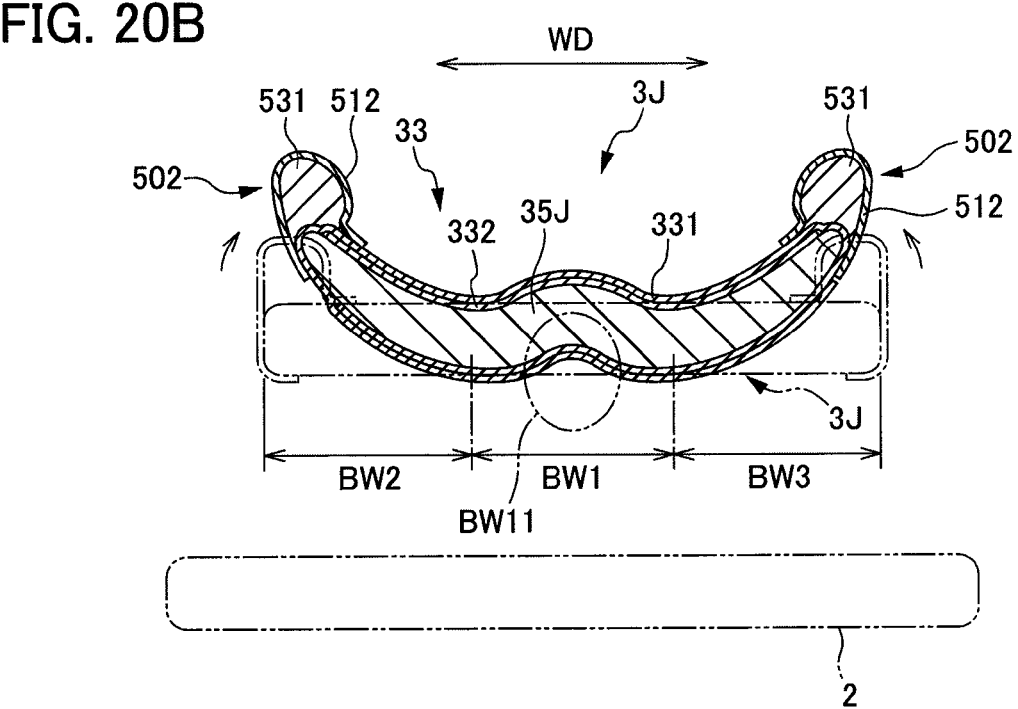
FIG. 20B is a magnified plan view near the handle part of the absorbent article according to the eighth embodiment of the present invention.
Figure 21:
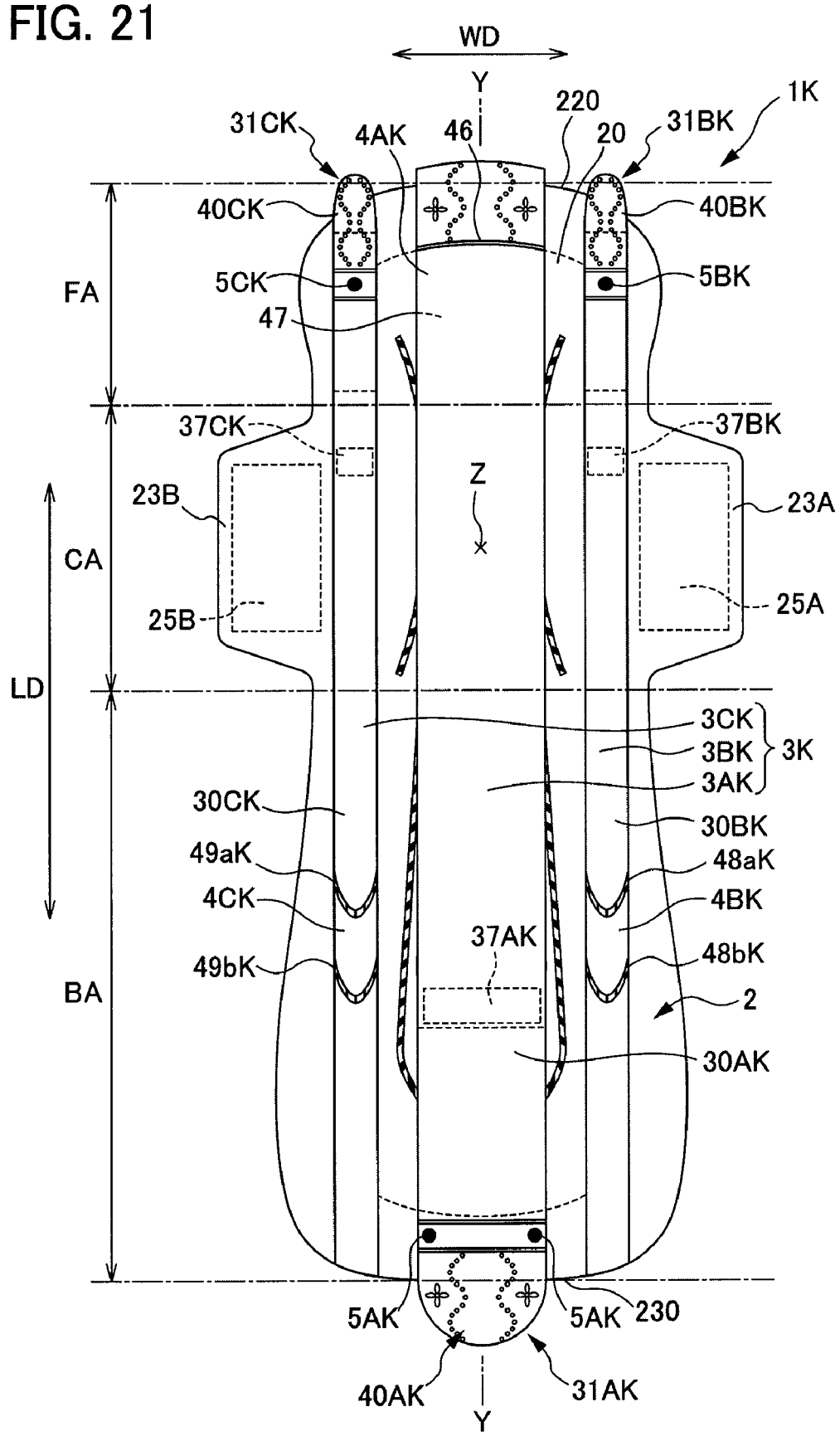
FIG. 21 is a lateral cross-sectional view of a top absorbent core of an absorbent article according to a ninth embodiment of the present invention.
Figure 22:
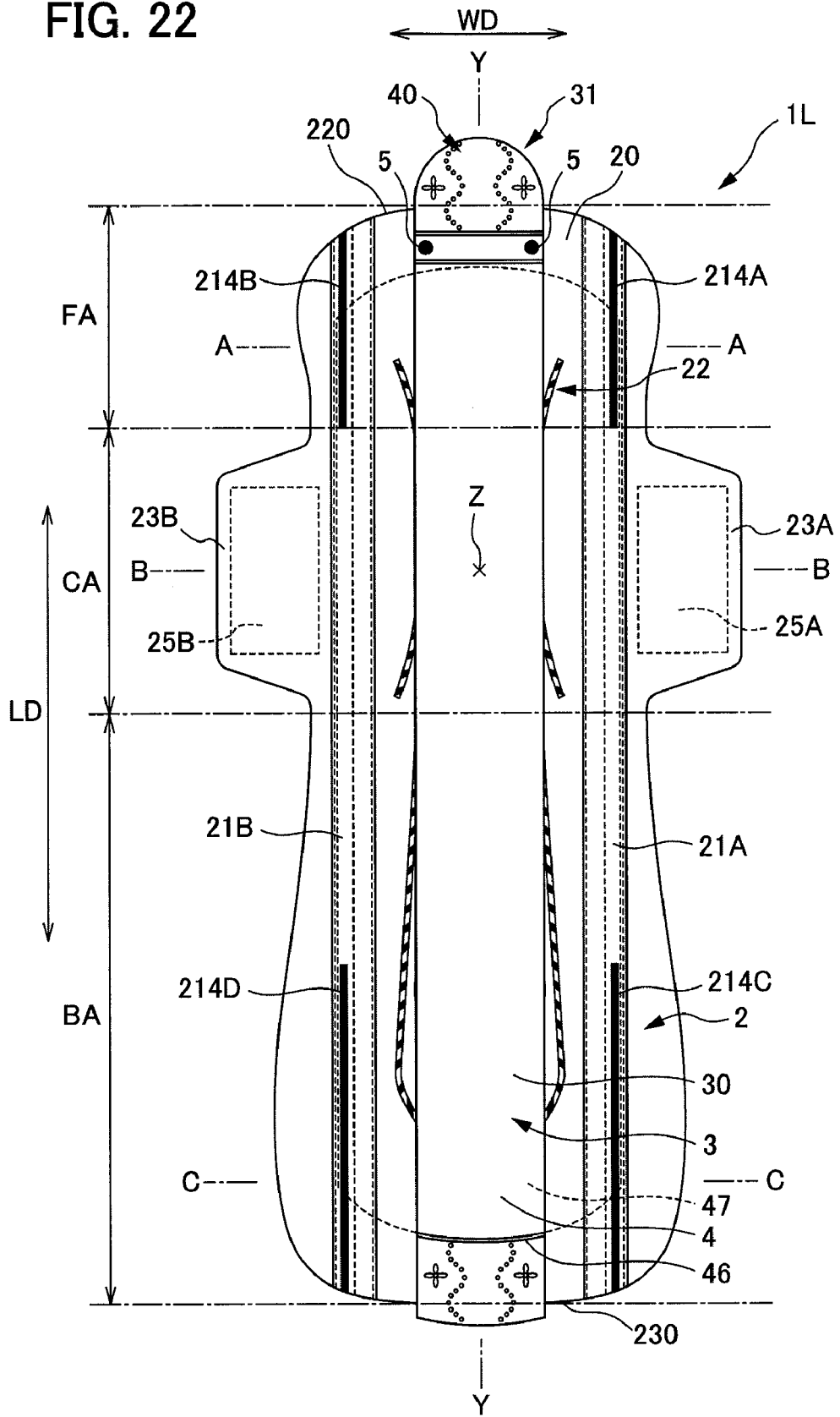
FIG. 22 is a plan view of an absorbent article according to a tenth embodiment of the present invention.
Figure 23:
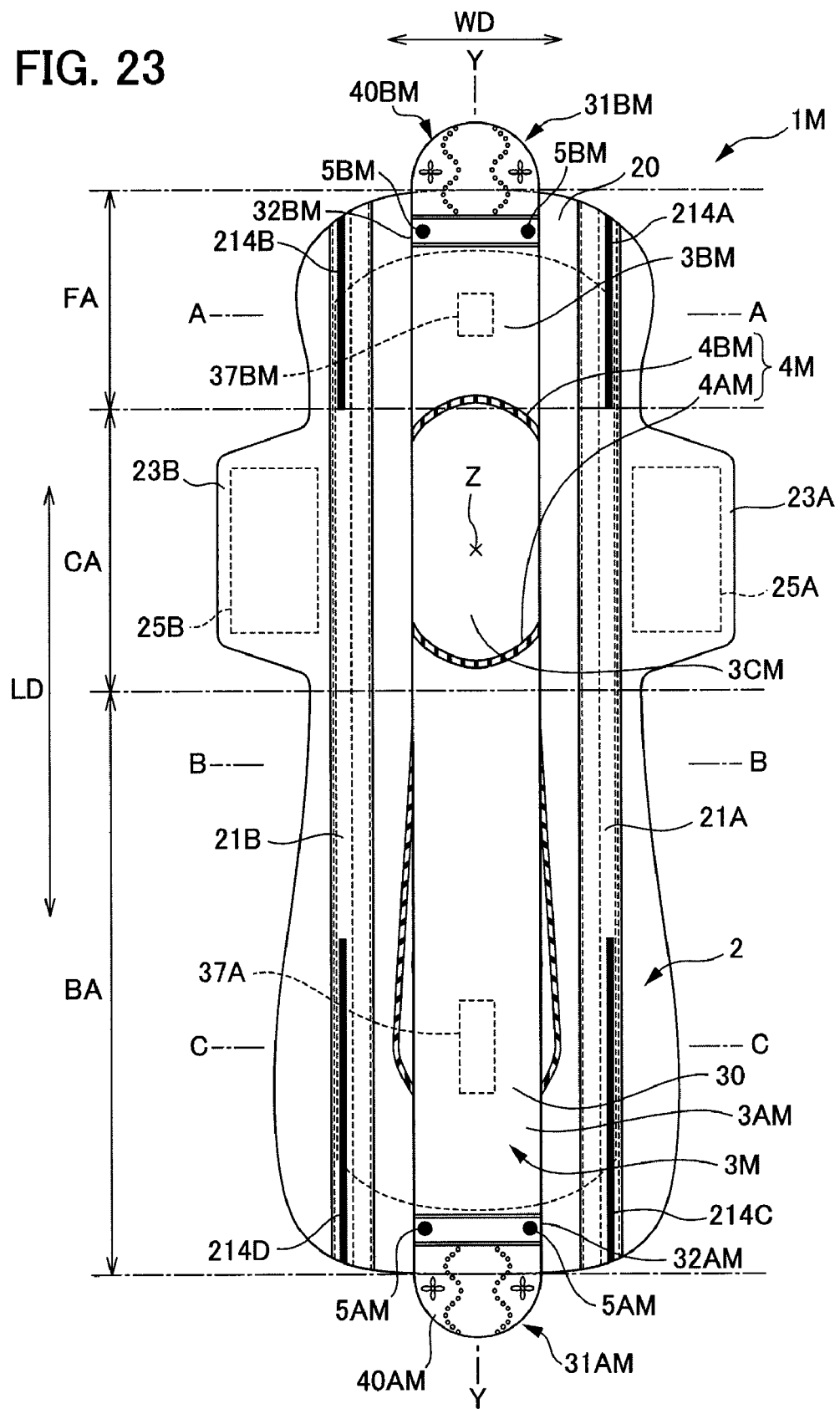
FIG. 23 is a plan view of an absorbent article according to an eleventh embodiment of the present invention.
Figure 24:
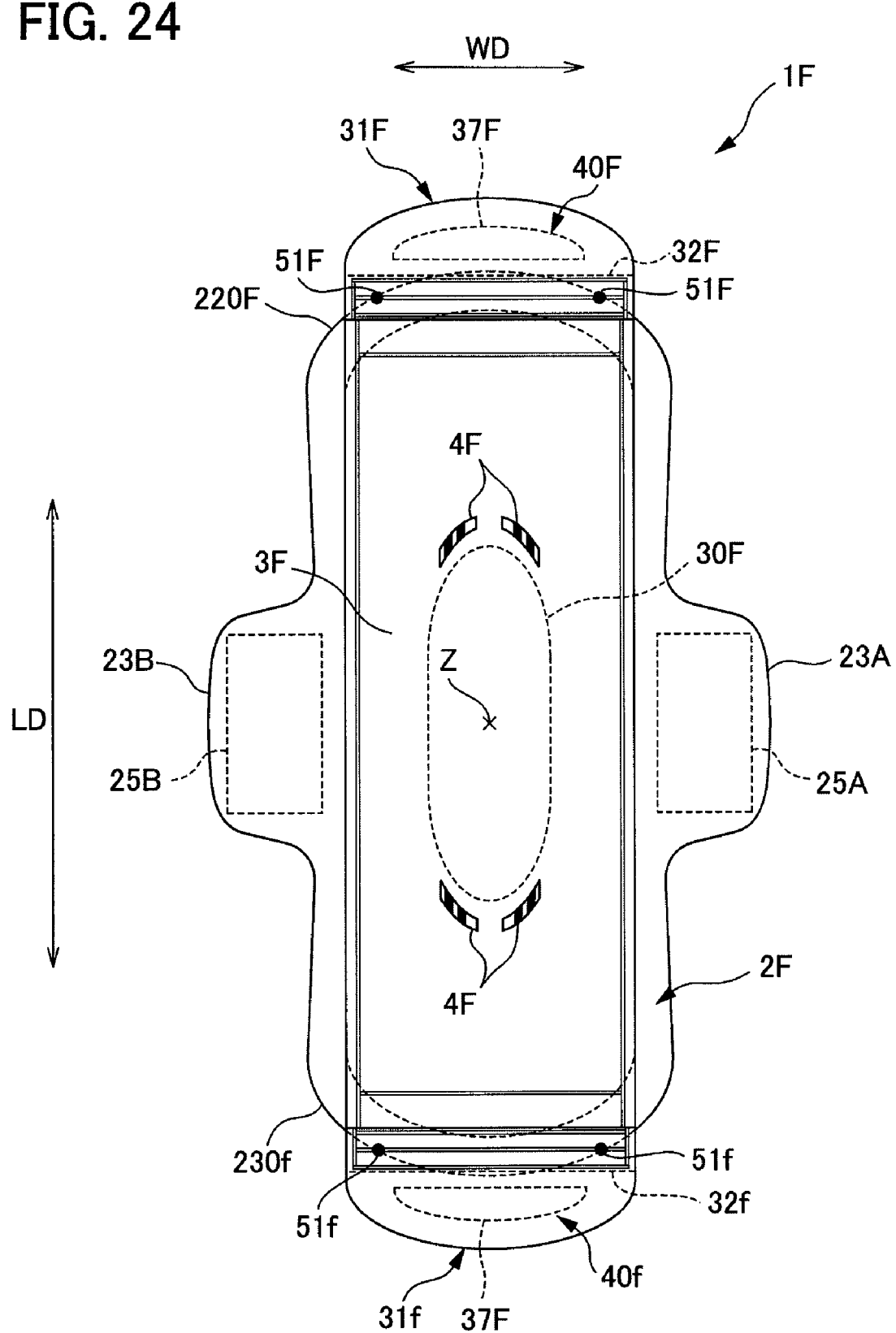
FIG. 24 is a plan view of an absorbent article of a twelfth embodiment of the present invention.

FIG. 12 is a plan view of an absorbent article according to a second embodiment of the present invention. FIG. 13 is a plan view of an absorbent article according to a third embodiment of the present invention. FIG. 14A is a longitudinal cross-sectional view of a top absorbent core according to a fourth embodiment of the present invention. FIG. 14B is a lateral cross-sectional view of the top absorbent core cut along the line (i)-(i) according to the fourth embodiment of the present invention. FIG. 14C is a lateral cross-sectional view of the top absorbent core cut along the line (ii)-(ii) according to the fourth embodiment of the present invention. FIG. 14D is a lateral cross-sectional view of the top absorbent core cut along the line (iii)-(iii) according to the fourth embodiment of the present invention. FIG. 15 is a plan view of an absorbent article according to a fifth embodiment of the present invention. FIG. 16 is a magnified longitudinal cross-sectional view near a fixing portion of the absorbent article according to the fifth embodiment of the present invention. FIG. 17 is a plan view of an absorbent article according to a sixth embodiment of the present invention. FIG. 18A is a lateral cross-sectional view of a top absorbent core of the absorbent article according to the sixth embodiment of the present invention. FIG. 18B is a lateral cross-sectional view of the top absorbent core of the absorbent article according to the sixth embodiment of the present invention. FIG. 19A is a plan view of an absorbent article according to a seventh embodiment of the present invention. FIG. 19B is a plan view of the absorbent article according to the seventh embodiment of the present invention. FIG. 20A is a magnified plan view near a handle part of an absorbent article according to an eighth embodiment of the present invention. FIG. 20B is a magnified plan view near the handle part of the absorbent article according to the eighth embodiment of the present invention. FIG. 21 is a lateral cross-sectional view of a top absorbent core of an absorbent article according to a ninth embodiment of the present invention. FIG. 22 is a plan view of an absorbent article according to a tenth embodiment of the present invention. FIG. 23 is a plan view of an absorbent article according to an eleventh embodiment of the present invention. FIG. 24 is a plan view of an absorbent article of a twelfth embodiment of the present invention.

1. First Embodiment

An absorbent article 1 according to the first embodiment of the present invention is described with reference to FIGS. 1 through 11.

1.1. Overview

As illustrated in FIGS. 1 through 11, the absorbent article 1 according to this embodiment is a substantially rectangular absorbent article. The absorbent article 1 is configured with an oblong base absorbent core 2, and an elongated top absorbent core 3 provided on one side of the base absorbent core 2 in the longitudinal direction LD of the base absorbent core 2. At least one part of the top absorbent core 3 in the longitudinal direction LD thereof is fixed to the base absorbent core 2, and remaining unfixed end portion is separated from the base absorbent core 2 starting at the fixed portion, serving as a free end 31 which is movable independently.

The base absorbent core 2 absorbs a predetermined fluid such as menstrual blood or the like that is not completely absorbed by the top absorbent core 3 which is provided on a garment side. A strip-shaped central region 20 is formed in the longitudinal direction LD on the surface of the base absorbent core 2 substantially in a center in the width direction WD of the base absorbent core 2. Wings 23A and 23B are formed at either side, respectively, in the width direction WD of the absorbent article 1.

Here, the absorbent article 1 has a position Z as a first position assumed to be where an excretory part of the wearer's body will make contact. The position Z is the intersection of a center line Y extending along the longitudinal direction LD at the center of the width direction WD of the absorbent article 1, with a center line B-B extending along the width direction WD at the center of the longitudinal direction LD of the wings 23A and 23B. In other words, the wings 23A and 23B are formed so as to satisfy the aforementioned positional relationship. In addition, it is assumed that an area of the base absorbent core 2 where the wings 23A and 23B are provided is a central area CA; that an area in front of the area where the wings 23A and 23B are provided is a front area FA; and that an area behind the areas where the wings 23A and 23B are provided is a back area BA. The details thereof will be described later.

The top absorbent core 3 is layered on the central region 20 of the base absorbent core 2. The top absorbent core 3 in use is in direct contact with an excretory part or the like of the wearer's body, and absorbs a predetermined fluid such as menstrual blood or the like. The top absorbent core 3 is fixed to the base absorbent core 2 by a fixing portion 4 provided in an area in the longitudinal direction LD thereof. In addition, an end portion on the side not fixed by the fixing portion 4 serves as a free end 31. If the top absorbent core 3 is fixed to the base absorbent core 2 at a position other than an end portion, for example, the side far from the fixing portion 4 in the longitudinal direction LD serves as the free end 31.

A handle part 40 is provided on the free end 31 side of the top absorbent core 3. In addition, when the absorbent article 1 is used, the handle part 40 is grasped, and the free end 31 side of the top absorbent core 3 is separated from the base absorbent core 2 starting at the fixing portion 4, allowing provision of the top absorbent core 3 along the gluteal cleft, which is a groove near the excretory part of the wearer's body.

Temporary fixing portions 5 are formed on the top absorbent core 3. The temporary fixing portions 5 temporarily lock the top absorbent core 3 to the base absorbent core 2, so as to allow separation by a predetermined force. The movement of the top absorbent core 3 is restricted while it is temporarily fixed by the temporary fixing portions 5, and not restricted when the temporary fixing is released. The top absorbent core 3 is separated from the base absorbent core 2 starting at the fixing portion 4, while the temporary fixing by the temporary fixing portions 5 is released.

The top absorbent core 3 also has a locking portion 37 on the handle part 40 side of the free end 31 in the longitudinal direction LD. After the top absorbent core 3 is separated from the base absorbent core 2 and the position thereof is adjusted so as to be along the gluteal cleft, the locking portion 37 locks the top absorbent core 3 to the base absorbent core 2 to keep the adjusted state.

The top absorbent core 3 is provided so as to be spaced apart from the base absorbent core 2 starting at the fixing portion 4. In other words, the top absorbent core 3 may be moved (shifted and deformed) independently of the base absorbent core 2. This allows an absorbent core to be continuously, tightly fit to the wearer's body without being affected by a movement of garment to which the base absorbent core 2 is provided. Individual components will be described hereinafter in detail.

1.2. Top Absorbent Core

As illustrated in FIG. 1 through FIG. 11, the top absorbent core 3 is an elongated absorbent core provided on a wearer's body contacting side of the base absorbent core 2. More specifically, the top absorbent core 3 is configured with a top absorbent portion 30, which may be provided so as to be along the central region 20 of the base absorbent core 2 and has an absorbent core 35, and an substantially plate-like handle part 40 provided on the free end 31 side. The top absorbent core 3 is fixed by the fixing portion 4 so that at least one edge in the longitudinal direction LD of the top absorbent core 3 serves as the free end 31. In addition, the end portion on the free end 31 side of the top absorbent portion 30 serves as a free end portion 32. The fixing portion 4 may be formed at an arbitrary position in the longitudinal direction LD of the top absorbent core 3; however, in this embodiment, when the top absorbent core 3 is provided on the base absorbent core 2, the fixing portion 4 is formed at one end side provided on a front edge 220 side. In addition, another end provided on a rear edge 230 side serves as the free end 31.

As illustrated in FIG. 4, the free end 31 may be spaced apart from the base absorbent core 2. The top absorbent core 3 is configured so that the free end 31 is able to be spaced apart therefrom starting at the fixing portion 4, from the state in which the top absorbent core 3 is provided substantially in a center in the width direction WD of the central region 20 of the base absorbent core 2. The free end 31 is an end portion far from the fixing portion 4. The longer the distance between the free end portion 32 and the fixing portion 4, the higher the degree of freedom of the top absorbent core 3.

Since the free end 31 is formed at a position separated a predetermined distance away from the fixing portion 4, it is possible to favorably adjust position of the top absorbent core 3 in an attached state by adjusting the position of the free end 31 side.

For example, the top absorbent core 3 is provided extending 5 mm in front of the front edge 220 of the base absorbent core 2, and 20 mm behind the rear edge 230 thereof. An extension of 5 mm in front of the front edge 220 is in consideration of dislocation in case of an error during manufacturing. In addition, the top absorbent core 3 is extended 20 mm behind the rear edge 230, allowing the handle part 40 to be easily grasped when grasping the handle part 40 to lift the free end 31 of the top absorbent core 3. Furthermore, the handle part 40 may be formed at the extended area.

As illustrated in FIGS. 3A, 3B, 3C, and FIG. 4, a top absorbent portion 30 is configured with a surface layer 33 provided on a skin contacting side, an absorbent core 35, and a back sheet 34 which serves as a leakage-preventing layer provided on a base absorbent core 2 contacting side of the top absorbent portion 30. The top absorbent portion 30 is a major component which absorbs a predetermined fluid excreted from an excretory part.

The surface layer 33 is formed through perforation processing carried out for a top sheet 331 and a second sheet 332 which are layered. The surface layer 33 is formed by forming multiple holes through the aforementioned perforation processing, and integrating the top sheet 331 and the second sheet 332. The second sheet 332 is provided covering the surface of a skin contacting side of the absorbent core 35.

The top sheet 331 is provided on the skin contacting side of the second sheet 332 so as to entirely cover the second sheet 332; the absorbent core 35, to be described later; and the back sheet 34. The top sheet 331 configures the outermost side of the top absorbent portion 30. The top sheet 331 is doubled on the base absorbent core 2 contacting side of the top absorbent portion 30. Note that the same component as a surface sheet 27 of the base absorbent core 2, which is described later, may be used for the top sheet 331.

As illustrated in FIG. 3A and FIG. 4, only the top sheet 331 is layered in three layers at the end on a front area FA side in the longitudinal direction LD of the top absorbent portion 30. In addition, the base absorbent core 2 and the fixing portion 4 to be fixed are provided at the end on the front area FA side. Note that it is preferable that each layer is joined using a hot melt adhesive in the area where the top sheet 331 is layered in three layers.

As illustrated in FIG. 3C and FIG. 4, the top sheet 331 and the back sheet 34 are layered in three layers by folding into three while they are layered at the end on the back area BA side in the longitudinal direction LD of the top absorbent portion 30. In addition, the handle part 40, to be described later, is provided at the end portion on the back area BA side. Moreover, each layer of the layered top sheet 331 and the back sheet 34 is joined using a hot melt adhesive at the end on the back area BA side.

The second sheet 332 is provided on a skin contacting side of the top absorbent portion 30 so as to cover the surface of the absorbent core 35, to be described later. In addition, the second sheet 332 is layered between the top sheet 331 and the absorbent core 35 to be described later.

It is preferable that the second sheet 332 is formed so as to be slightly larger than the absorbent core 35. In this embodiment, the length in the longitudinal direction LD of the second sheet 332 is 300 mm, and the length in the width direction WD is 45 mm.

In addition, the second sheet 332 according to this embodiment is an air-through non-woven fabric made of fibers of 3.3 dtex and 51 mm fiber length, which is formed of core-insheath fiber configured with polypropylene as a core and polyethylene as a sheath. The basis weight of the second sheet 332 is 20 g/m², for example. It is preferable that the second sheet 332 be formed so that the density is higher than the top sheet 331. A density of the second sheet 332 being higher than the top sheet 331 allows improvement in liquid transitivity from the top sheet 331. In addition, a density gradient may be provided by layering the top sheet 331 in two layers instead of the second sheet 332.

Moreover, as illustrated in FIG. 3C and FIG. 4, the top absorbent portion 30 is configured with a liquid impermeable back sheet 34 serving as a leakage-preventing layer. The back sheet 34 is provided on the rear edge 230 side and is at least a part of a base absorbent core contacting side of the absorbent core 35.

As illustrated in FIG. 3C, it is preferable that the back sheet 34 be provided at a lateral side of the base absorbent core contacting side of the absorbent core 35, not on the skin contacting side. As a result, when the predetermined fluid excreted onto the top absorbent portion 30 flows into the rear edge 230 side, the absorbent core 35 may absorb the fluid. A liquid impermeable film with a basis weight of 24 g/m² or an SMS non-woven fabric or the like made up of three layers of spun-bonded, melt blown, and spun-bonded hydrophobic fibers may be used as the back sheet 34.

The absorbent core 35 mainly absorbs and holds excreted predetermined fluid. The absorbent core 35 is made of crushed pulp and highly absorbent polymer. Here, it is preferable that the crushed pulp be provided so that the basis weight is partially different at the top absorbent core 30. More specifically, as illustrated in FIG. 5, the basis weight of an area 353 where the fixing portion 4 is formed is 200 g/m², and the basis weight of areas 354, 355, and 356 between the fixing portion 4 and the free end portion 32 is 500 g/m².

In addition, as illustrated in FIG. 5, nondense portions 351 and 352 are formed in the back area BA of the top absorbent portion 30. The nondense portion 351 is formed on the central area CA side of the back area BA of the top absorbent portion 30 along the width direction WD; and the nondense portion 352 is formed on the rear edge 230 side of the back area BA of the top absorbent portion 30 along the width direction WD.

The nondense portions 351 and 352 are areas where the basis weight of crushed pulp is lower than in other areas. In addition, the nondense portions 351 and 352 are folding starting points when folding the absorbent article. Here, a vicinity of a free end refers to an area from the outer edge of the handle part 40 to one third of the total length of the top absorbent core 3, including the handle part 40.

This suppresses generation of wrinkles due to a difference in curvature between a folded inside and outside when the absorbent article 1 is folded for individual packaging or the like.

Moreover, an oblong area 357 with a basis weight of 200 g/m² is formed substantially in a center in the width direction WD of the top absorbent portion 30 in an 80-mm long area 357, from a position slightly toward the free end portion 32 side from the position Z to the free end portion 32. The area 357 guides deformation of the top absorbent core 3 in an attached state.

The absorbent core 35 is formed so that the length in the longitudinal direction LD is shorter than the length in the longitudinal direction LD of the top sheet 331. In other words, as mentioned above, the absorbent core 35 is not provided at both ends in the longitudinal direction LD of the top absorbent portion 30.

It is desirable that the length in the longitudinal direction LD of the top absorbent core 3 is, for example, from 200 mm to 500 mm, preferably 230 mm to 450 mm. The length in the longitudinal direction LD of the top absorbent portion 30, according to the first embodiment, may be exemplified as 335 mm, for instance. In this embodiment, the length in the longitudinal direction LD of the top absorbent portion 30 may be exemplified as 280 mm, for instance.

In addition, in this embodiment, the length in the width direction WD of the top absorbent portion 30 is shorter than the length in the width direction WD of the base absorbent core 2. It is also preferable that the top absorbent portion 30 has a length allowing contact in the longitudinal direction LD along the gluteal cleft.

More specifically, it is desirable that the length in the width direction WD of the top absorbent portion 30 be from 15 mm to 50 mm, and preferably, from 20 mm to 40 mm. If the width dimension is less than 15 mm, the width is not enough to continuously make contact with the vaginal opening, generating a gap between the wearer's body and the sanitary napkin, and easily causing leakage. The width dimension of the top absorbent portion 30, according to the first embodiment, may be exemplified as 40 mm, for instance.

In addition, it is preferable that the width of the top absorbent portion 30 be almost equal in the longitudinal direction LD. Moreover, it is preferable that a cross-sectional shape in the width direction WD of the top absorbent portion 30 indicate that the skin contacting side and the base absorbent core 2 contacting side are at least almost in parallel.

1.3. Fixing Portion

As illustrated in FIG. 1 and FIG. 4, the fixing portion 4 is provided at an arbitrary position of the top absorbent core 3, and fixes the top absorbent core 3 to the base absorbent core 2. More specifically, a predetermined area in the longitudinal direction of the top absorbent core 3 is fixed to the base absorbent core 2 by the fixing portion 4. In the top absorbent core 3, an end portion which is not fixed by the fixing portion 4 serves as a free end.

As illustrated in FIG. 1 and FIG. 4, the fixing portion 4 is formed on the front edge 220 side of the top absorbent core 3, while the top absorbent core 3 is mounted on the base absorbent core 2. More specifically, it is formed at an end portion on the front edge 220 side of the top absorbent portion 30, which is a position corresponding to a region from an area formed only by the top sheet 331 to the area 353, where the basis weight of the absorbent core 35 is 200 g/m².

The fixing portion 4 is configured with a pressure-bonding portion 46 and a joining portion 47. The joining portion 47 is formed by providing a hot-melt adhesive to the area formed only by the top sheet 331 and an area where the absorbent core 35 is provided along the longitudinal direction LD at almost even intervals, and mounting and joining the top absorbent core 3 substantially in a center in the width direction WD of the front area FA of the base absorbent core 2. It is preferable that the hot-melt adhesive be attached opposite to an area where compressed grooves 22 are not provided on the front area FA of the base absorbent core 2. In addition, the hot-melt adhesive is attached to an area from a predetermined position between the position Z and the front edge 220 to the front edge 220. In other words, the fixing portion 4 is formed at a position closer to the front edge 220 side than the position Z. Note that the fixing portion 4 may integrate and join the top absorbent core 3 and the base absorbent core 2 by way of compressed grooves instead of the hot-melt adhesive. In this case, the area where the base absorbent core 2 and the top absorbent core 3 are fixed by the compressed grooves is the fixing portion 4.

The pressure-bonding portion 46 is formed on the front edge 220 side of the base absorbent core 2 in an area where the absorbent core 28 is not provided. The pressure-bonding portion 46 is formed in the area formed only by the top sheet 331 of the top absorbent portion 30 and in the aforementioned area of the base absorbent core 2.

The fixing portion 4 is formed by joining the surface layer 33 and the absorbent core 35 of the top absorbent core 3 to the base absorbent core 2 through a pressure-bonding process to integrate them.

1.4. Temporary Fixing Portion

As illustrated in FIG. 1, temporary fixing portions 5 are formed in the top absorbent core 3. The temporary fixing portions 5 temporarily lock the top absorbent core 3 to the base absorbent core 2 so as to be spaced apart from each other using a predetermined force. The movement of the top absorbent core 3 is restricted while it is temporarily fixed by the temporary fixing portions 5, and not restricted when the temporary fixing is released. The top absorbent core 3 is separated, starting at the fixing portion 4, from the base absorbent core 2, while the temporary fixing by way of the temporary fixing portions 5 is released. The temporary fixing portions 5 are formed between the fixing portion 4 and the free end portion 32 of the top absorbent core 3. In addition, they are formed near the rear edge 230 of the central region 20 of the base absorbent core 2.

More specifically, the temporary fixing portions 5 are formed near the free end 31 of the top absorbent core 3. Moreover, the temporary fixing portions 5 are formed on both sides in the width direction WD of the free end portion 32.

The temporary fixing portions 5 are formed in an area formed only by the top sheet 331 and the back sheet 34 of the top absorbent core 3. Moreover, the temporary fixing portions 5 are formed near the handle part 40 of the top absorbent core 3. A force attached in the outward longitudinal direction LD of the handle part 40 or upper surface direction of FIG. 1 is directly transferred to the temporary fixing portions 5. In other words, when the handle part 40 is shifted in the outward longitudinal direction LD or upper surface direction of FIG. 1, the temporarily fixed state by the temporary fixing portions 5 is released.

As mentioned above, the temporary fixing portions 5 are formed into a circle at either side, respectively, in the width direction WD of the free end portion 32 near the handle part 40 of the top absorbent core 3. The top absorbent core 3 is fixed at points by two temporary fixing portions 5 and 5.

In the base absorbent core 2, the temporary fixing portions 5 are formed on the rear edge 230 side of the base absorbent core 2. The temporary fixing portions 5 are formed in an area formed only by the surface sheet 27 and the back sheet 29 of the base absorbent core 2.

The temporary fixing portions 5 are formed through an embossing process (pressure-bonding process) from the upper surface of the top absorbent core 3, while the top absorbent core 3 is layered on the base absorbent core 2.

More specifically, the temporary fixing portions 5 are formed by pressure-bonding the free end portion 32 of the top absorbent core 3, formed only by the top sheet 331 and the back sheet 34; and an area of the base absorbent core 2 where the surface sheet 27 and the back sheet 29 are layered; while heating using an embossed member on the surface of which irregularities are formed. Accordingly, the temporary fixing portions 5, which are embossed parts, fix the top absorbent core 3 and the base absorbent core 2 through mild thermal bonding.

Here, a joining force of the temporary fixing portions 5 is strong enough that the free end 31 of the top absorbent core 3 and the base absorbent core 2 are not easily separated in an attaching process to the wearer's body. Moreover, the joining force is strong enough that a user may easily release it without any complicated operations.

In addition, the locking portion 37 may also serve as the temporary fixing portions 5. In other words, the locking portion 37 may serve as the temporary fixing portions 5 by locking it onto the base absorbent core 2 before attaching to the wearer's body. In other words, the movement of the free end 31 of the top absorbent core 3 may be restricted by locking the locking portion 37 as a temporary fixing portion to the base absorbent core 2.

In addition, both of the temporary fixing portions 5 and the locking portion 7 may be used for locking by further providing the locking portion 37 which serves as a temporary fixing portion in addition to the aforementioned temporary fixing portions 5.

1.5. Handle Part

As illustrated in FIG. 1 and FIG. 4, the handle part 40 is provided on the free end 31 side in the longitudinal direction LD of the top absorbent core 30. The handle part 40 is a part which is held and pulled by a user to adjust the position of the top absorbent core 3 in the attaching process of the absorbent article 1. The handle part 40 is formed so as to protrude to the outermost side in the longitudinal direction LD of the central region in the width direction WD thereof.

The outer edge region of the handle part 40 is in a curved line. More specifically, it may be formed so as to be in an approximate semicircle having the intersection between the extended line substantially in a center in the width direction WD of the top absorbent core 3 and the outer edge as its apex.

The handle part 40 is provided on the free end 31 side, and is formed in an area on the free end 31 side of the top absorbent portion 30 where there is no absorbent core 35 and only the top sheet 331 and the back sheet 34 extend.

The handle part 40 is formed by increasing rigidity of the free end portion 32 of the top absorbent portion 30. More specifically, the handle part 40 is formed by embossing the free end portion 32 of the top absorbent portion 30 or area where only the top sheet 331 and the back sheet 34 extend, so as to increase the rigidity thereof. Small circular embossed portions are formed into a gourd shape at the handle part 40, and flower-shaped embossed portions are formed at the lateral part thereof. The embossed portions formed into a gourd shape serve as guiding elements for positions at which fingers are placed to grasp the handle part 40. Design characteristics may be given to the handle part 40 by devising the shape of the embossed portions. In other words, a guide element and a design may be formed on the handle part 40 through the embossing process to provide rigidity. In other words, it is possible to give a predetermined function and a design property simultaneously in a rigidity providing process.

A design (guide element) to be provided on the handle part 40 may be arbitrarily provided according to the shape of the embossed portions. For example, an indicator which encourages a user to hold and pull the handle part 40 in a predetermined direction along the longitudinal direction LD may be provided. More specifically, an arrow, which points to the outer side in the longitudinal direction LD, suggesting pulling the handle part 40 in the longitudinal direction LD, a point, which indicates a holding position, or a combination of predetermined colors, may be provided.

In addition, irregularities are formed on the surface of the handle part 40 through the embossing process performed on the handle part 40. The irregularities may be a clue for a user to find the handle part 40, which is provided at a position hidden from the user in an attaching process of the absorbent article 1.

As mentioned above, the temporary fixing portions 5 and 5 are formed near the handle part 40. Since the temporary fixing portions 5 and 5 are formed at positions which follow the movement of the handle part 40, a temporarily fixed state of the temporary fixing portions 5 and 5 is released by shifting the handle part 40 only a predetermined distance. More specifically, the temporarily fixed state of the temporary fixing portions 5 and 5 is released by shifting the handle part 40 to lock the locking portion 37 to be described later to another position.

In addition, the locking portion 37 to be described later is provided near the handle part 40. The locking portion 37 is provided at a position which shifts following the movement of the handle part 40. In other words, the handle part 40 is provided at a position allowing favorable adjustment of the shifting (position) of the locking portion 37.

In addition, the handle part 40 is provided protruding outward from the rear edge 230 of the base absorbent core 2. The region of the handle part 40 protruding outward from the rear edge 230 preferably serves as a grasping part. However, an end portion on the rear edge 230 side of the handle part 40 should not protrude from the base absorbent core 2, and may be provided further on the inside than the rear edge 230 of the base absorbent core 2.

It is preferable that the outer edge of the handle part 40 is provided so as to extend from the rear edge 230 of the base absorbent core 2. More specifically, a range from 100 mm outward to 50 mm inward, preferably from 60 mm outward to 30 mm inward, and more preferably from 30 mm outward to 20 mm inward may be exemplified. Provision of the outer edge region of the handle part 40 so as to extend from the rear edge 230 of the base absorbent core 2 makes it easier for a user to hold the handle part 40. For example, it is easier for a user to recognize the handle part 40 when searching for the handle part 40 with a hand behind thereof at the time of attaching of the absorbent article 1. In addition, a region protruding outward from the rear edge 230 of the handle part 40 preferably serves as a grasping part.

The flexural rigidity (B) of the handle part 40 is from 0.1 to 1.2 ($10^{-4}$N·m²/m), preferably from 0.2 to 1 ($10^{-4}$N·m²/m), and more preferably from 0.3 to 0.8 ($10^{-4}$N·m²/m). If the flexural rigidity (B) of the handle part 4 is lower than 0.1 ($10^{-4}$N·m²/m), for example, it may be difficult to perform a predetermined operation such as grasping the handle part 40 and providing the top absorbent core to a predetermined region of the wearer's body. On the contrary, if the flexural rigidity (B) of the handle part 40 is higher than 10, for example, the handle part 40 may bring discomfort during use. It is preferable that the flexural rigidity (B) of the handle part 40 fall within the aforementioned range.

The flexural recovery property (2HB) of the handle part 40 is 10 ($10^{-2}$N·/m) or less, preferably 7 or less, and more preferably 3 ($10^{-2}$N·/m) or less. If the flexural recovery property (2HB) of the handle part 40 is higher than 10 ($10^{-2}$N·m/m), it is easy to make a crease when the handle part 40 is folded back partway, possibly causing discomfort due to the crease. Therefore, it is preferable that the flexural recovery property (2HB) of the handle part 40 fall within the aforementioned range.

It is preferable that the thickness of the handle part 40 be from 0.5 to 4 mm, and preferably from 0.7 to 3.5 mm. If the handle part 40 is thinner than 0.5 mm, a user may worry that the handle portion may be torn when the user grips and pulls the handle portion 40. On the contrary, if the handle part 40 is thicker than 5 mm, the handle portion 40 may give a user a sensation of a foreign-object during use.

Measuring Method

Measuring method of the flexural rigidity (B) and the flexural recovery (hysteresis: 2HB) is described hereinafter.

An automatic pure bending tester manufactured by Kato Tech Co., Ltd. (model name KES-FB2-AUTO-A) was used as a measuring device. A size of a sample used for the measurement was adjusted to 100 mm by 100 mm (in a case where a sufficient width cannot be obtained, the width was adjusted to between 10 mm to 100 mm by 10 mm intervals).

The sample is bent toward an obverse side to a maximum curvature of 2.5 cm$^{-1}$, by pure bending that maintains an arc on one side, with a chuck interval of 1 cm and released.

Thereafter, the specimen is bent toward a reverse side to a maximum curvature of −2.5 cm$^{-1}$ and released. Then a relation between a curvature and a bending moment is evaluated.

The flexural rigidity (B) is obtained as a value on a hysteresis curve, and is represented by an average tilt angle of curvatures of from 0.5 to 1.5 cm$^{-1}$.

The flexure recovery (2HB) is represented by a hysteresis width of a bending moment M at a curvature of 1.0 cm$^{-1}$. Greater flexure recovery (2HB) signifies worse (lower) flexure recovery.

1.6. Locking Portion

As illustrated in FIGS. 1 and 4, the absorbent article 1 is configured with the locking portion 37 as a locking means, and the central region 20 of the base absorbent core 2 as a to-be-locked body. The locking portion 37 locks the free end 31 side of the top absorbent core 3 at a predetermined position. More specifically, the locking portion 37 locks the free end 31 side of the top absorbent core 3 to a predetermined position when it is attached to the wearer's body as an attaching target.

The locking portion 37 is provided on the free end 31 side of the top absorbent core 3. More specifically, the locking portion 37 is provided on the base absorbent core 2 side of the top absorbent core 3, or the back area BA.

More specifically, as illustrated in FIG. 5, the locking portion 37 is provided between the nondense portion 351 of the absorbent core 35 provided substantially in a center in the longitudinal direction LD of the top absorbent portion 30, and the nondense portion 352 provided on the back area BA side. Even more specifically, it is provided so that the end portion on the rear edge 230 side of the locking portion 37 is close to the end portion on the front edge 220 side of the nondense portion 352.

The position of the locking portion 37 is adjusted according to the to-be-locked body. If the locking portion 37 is locked to underwear as a garment which is provided so as to cover the absorbent article 1, the locking portion 37 may be provided near the free end 31 or the handle part 40. In addition, in the case of locking to the wearer's body, it is possible to provide the locking portion 37 on the skin contacting side of the top absorbent portion 30 near the top absorbent portion 30, or near the free end 31 of the handle part 40.

Note that the locking portion 37 may be provided on both the top absorbent portion 30 side and the free end portion 32 side. In this case, it is possible to select whether to lock the locking portion 37 to any one of the base absorbent core 2, underwear, or the wearer's body, at the time of attaching. In addition, as mentioned above, the position and the number of the locking portion 37 to be provided may be adjusted arbitrarily. Moreover, in the above description, while a configuration of when the locking portion 37 is locked to the base absorbent core 2 is described, the locking portion 37 may be locked to underwear even with this configuration.

A suitable member corresponding to an assumed to-be-locked body may be selected as a member for forming the locking portion 37. For example, it is preferable that the member to be used is an adhesive material when assuming locking to the wearer's body. A hot-melt adhesive or a gel adhesive may be exemplified as the adhesive material to be used.

In addition, when assuming locking to underwear or the base absorbent core 2, hook material in addition to the aforementioned adhesive material may be used as a member (material) for the locking portion 37. When the hook material is used as a member for the locking portion 37, the hook material may be engaged and locked to a to-be-locked member, which is provided at a position corresponding to the position at which the locking portion is locked, underwear, or fiber of the surface material of the base absorbent core 2.

A male material for a surface fastener may be exemplified as the hook material. In this embodiment, it is preferable that multiple pins of the hook material, which engage with fibers, have predetermined directionality. Having directionality means that multiple pins of the hook material are fixed to a substrate of the hook material while they are tilted at a predetermined angle.

The hook material having directionality should be engaged by pressing the hook material against the to-be-locked body. The movement of the hook material is restricted in a predetermined direction in which the pins tilt, and movement thereof is not restricted in the opposite direction to the direction in which the pins tilt. In other words, when pulled in the direction in which the pins tilt as a predetermined direction, the hook material is not shifted, and engagement is released and shifted when parallel movement is performed in the opposite direction of the direction in which the pins tilt as a predetermined direction.

When the hook material having directionality is used as the locking portion 37, the hook material should be provided so that the tilting direction of the multiple pins faces the fixing portion 4 side of the top absorbent core 3. Accordingly, when the top absorbent core 3 and the locking portion 37 make contact with the base absorbent core 2, the locking portion 37 is pulled in a direction to which the pins tilt due to tension from curvature of the base absorbent core 2, and locked, thereby restricting the movement thereof. In addition, when the top absorbent core 3 is pulled outward, the locking portion 37 is pulled in the opposite direction to the direction in which the pins tilt, and the lock is released and shifted.

Note that it is preferable that a locking force of the locking portion 37 not be weakened even if lock and release are repeated a plurality of times. A to-be-locked body suitable for a member used for the locking portion 37 may be provided in an area in the base absorbent core 2 with which the locking portion 37 is assumed to make contact. This allows prevention of decrease in locking force due to repetitive lock and release of the locking portion 37. For example, when an adhesive material is used for the locking portion 37, a mold release film may be provided. It is possible to prevent decrease in adhesive force due to fibers attached to the locking portion 37 by making the mold release film make contact with the locking portion 37 before attaching.

In addition, when hook material is used for the locking portion 37, for example, a female material of the hook material may be provided in an area in the base absorbent core 2 to which the locking portion 37 makes contact before attaching to the wearer's body. The locking force of the hook material is rarely weakened even if lock and release are repeated a plurality of times; however, the pins configuring the hook material may fall out when lock is released or fibers in an area with which the hook material makes contact may be damaged. Provision of the female material of the hook material in an area with which the locking portion 37 makes contact before attaching of the absorbent article 1 allows prevention of removal of the pins of the hook material and damage to the fibers in an area with which the hook material makes contact.

1.7. Base Absorbent Core

As illustrated in FIGS. 1, 3A, B, and C, and FIG. 4, the base absorbent core 2 is formed into a substantially rectangular shape, and is configured with a liquid permeable surface sheet 27, a liquid impermeable back sheet 29, and a liquid retentive absorbent core 28, provided between the surface sheet 27 and the back sheet 29. In the base absorbent core 2, a strip-shaped central region 20 is formed along the longitudinal direction LD substantially in a center in the width direction WD of the base absorbent core 2. The top absorbent core 3 is provided in the central region 20. In addition, gathers 21A and 21B are formed on either side in the width direction WD of the central region 20. The gathers 21A and 21B make contact with groin area, and control leakage of menstrual blood or the like that flows through the surface of the wearer's body but is not absorbed by the top absorbent core 3. In addition, the wings 23A and 23B are formed at either side in the width direction WD of the absorbent article 1, so as to protrude outward in the width direction WD.

Moreover, as illustrated in FIG. 2, a dislocation preventing part 26 is provided substantially in a center in the width direction WD of the back side, which is another side of the base absorbent core 2. Wing side dislocation preventing parts 25A and 25B are provided at the back sides of the wings 23A and 23B.

The central region 20 is formed in a strip shape along the longitudinal direction LD substantially in a center in the width direction WD of the base absorbent core 2. The central region 20 is a thin area configuring a base absorbent layer. The central region 20 is configured with the surface sheet 27, the back sheet 29, and the absorbent core 28. The surface sheet 27 and the absorbent core 28 are joined using a hot-melt adhesive, and adhesively folded by multiple compressed grooves 22 formed along the longitudinal direction LD.

In this embodiment, the surface sheet 27 in the central region 20 is formed of an air-through non-woven fabric with a basis weight of 30 g/m$^2$. In addition, the non-woven fabric is formed of fibers configured with polypropylene as a core and polyethylene as a sheath of 2.2 dtex and 51-mm fiber length. Note that it is preferable that the surface of the fibers be coated with a hydrophilic oil solution.

The absorbent core 28 is formed by layering crushed pulp mixed with a highly absorbent polymer, and covering it with tissue paper (not shown in the drawing). 15 g/m$^2$ of the tissue paper is used, for example. As illustrated in FIG. 6, it is preferable that the crushed pulp is provided so that the basis weight is different depending on the location in the central region 20. The crushed pulp may be layered so as to be 500 g/m$^2$ in an area 201 at the peripheral border including the position Z. In addition, the crushed pulp is layered so as to be 100 g/m$^2$ in areas 202 at either side in the longitudinal direction LD of the area 201. Moreover, the crushed pulp is layered so as to be 100 g/m$^2$ in an area 203, which is formed on the rear edge 230 side of the area 201 along the longitudinal direction LD. Furthermore, an area 204 where the crushed pulp is 300 g/m² is formed on the front edge 220 side of the area 201 in the longitudinal direction LD. It is possible to layer the crushed pulp so as to be 200 g/m² in another area 205. In addition, the highly absorbent polymer is mixed so that the average basis weight of the entire absorbent core 28 becomes 10 g/m²; however, it is distributed in proportion to the basis weight of the crushed pulp in each region of the absorbent core 28. The reason is that the highly absorbent polymer is uniformly distributed with the crushed pulp.

As illustrated in FIG. 7, the compressed grooves 22 are formed in the central region 20. The compressed grooves 22 are formed by providing high-compressed portions and low-compressed portions alternatingly in the longitudinal direction LD. In addition, the compressed grooves 22 are formed from the front area FA to the back area BA of the central region 20. The length of the compressed grooves 22 in the width length WD may be exemplified as 2 mm. In addition, an interval between adjacent compressed grooves 22 in the width direction WD may be exemplified as 4 mm.

As illustrated in FIG. 7, six compressed grooves are formed in the front area FA. Compressed grooves 223 to be described later are formed on the outer side in the width direction WD. The compressed grooves 223 are described later. Compressed grooves 221, 221 are formed on the inner side in the width direction WD of the compressed grooves 223, 223. The compressed grooves 221, 221 are formed between the front area FA and the back area BA, and connected to each other at the back area BA. The compressed grooves 221, 221 then continue and form compressed grooves in a U shape protruding to the rear edge 230 side. Compressed grooves 222, 222 are formed on the inner side in the width direction WD of the compressed grooves 221, 221. The compressed grooves 222, 222 are formed in lines between the front area FA and the central area CA.

An end portion of a compressed groove 224 to be described later in addition to the aforementioned six compressed grooves 221, 222, and 223 are formed in the central area CA. The compressed grooves 223 are formed between the front area FA and the central area CA, in a gentle curve protruding inward in the width direction WD. The compressed grooves 223, 223 are formed so that the interval therebetween become the narrowest at a position corresponding to the position Z in the longitudinal direction LD. At this position, the aforementioned six compressed grooves 221, 222, and 223 are formed at almost even intervals in the width direction WD. The compressed groove 224 is described later.

The compressed groove 224, a compressed groove 226, and compressed grooves 227, 227 are formed in the back area BA in addition to the compressed grooves 221 continuously formed from the aforementioned front area FA.

The compressed groove 224 is formed on the outside of the compressed grooves 221. More specifically, it is formed so as to enclose the compressed grooves 221 which are formed in a U shape.

The compressed groove 226 is formed inside of the compressed grooves 221 so as to extend in the width direction WD. More specifically, the compressed groove 226 is formed so as to connect the compressed grooves 221, 221 to each other, which are separated in the width direction WD on the central area CA side of the back area BA. The curve of the compressed groove 226 is formed in a relaxed U shape protruding to the rear edge 230 side in the longitudinal direction LD.

The compressed grooves 227, 227 are formed in an area enclosed by the compressed grooves 221 and the compressed groove 226 so as to extend in the longitudinal direction LD.

Three compressed grooves which are formed so as to cross in the width direction are formed in the back area BA. In other words, three compressed grooves are formed in the longitudinal direction LD at the center in the width direction WD.

Since such compressed grooves 22 are integrally formed by compressing the absorbent core 28 and the surface sheet 27, a predetermined rigidity is attached to the central region 20. It is possible to prevent dislocation of the position of the top absorbent core 3 when the absorbent article 1 is fixed to underwear and lifted up in relation to the rigidity of the top absorbent core 3. In other words, if the rigidity of the base absorbent core 2 is too low compared to the rigidity of the top absorbent core 3, the top absorbent core 3 cannot follow bending of the base absorbent core 2, thereby preventing dislocation of the position of the top absorbent core 3.

As illustrated in FIG. 1 and FIGS. 3A, B, and C, the gathers 21A and 21B are provided at either side of the central region 20 along the longitudinal direction LD. The gathers 21A and 21B are formed so that at least a part thereof rises up in the thickness direction.

The gathers 21A and 21B according to this embodiment are provided at positions along the longitudinal direction LD approximately 64 mm apart from the center in the width direction WD of the central region 20, respectively. The gathers 21A and 21B are fixed at base portion thereof, and have end portions 215A and 215B moveable in the thickness direction. The end portions 215A and 215B make contact with the groin area of the wearer's body in an attached state.

The gathers 21A and 21B are parts folded into two so that non-woven fabrics of a predetermined size that are more hydrophobic than the surface sheet 27 of the central region 20 are adhesively folded to each other. Elastic members 213A and 213B are provided between (inside) the folded non-woven fabrics.

In this embodiment, three of the elastic members 213A and 213B are provided at almost even intervals. The elastic members 213A and 213B are formed of 470 dtex thread rubber, for example, and fixed while it is elongated approximately 1.3 times. A stretching force of the elastic members 213A and 213B allows rising up of the gathers 21A, 21B.

Both end portions in the longitudinal direction LD of the gathers 21A, 21B are folded back outward in the width direction WD, and fixed by the hot-melt adhesives 214A, 214B, 214C, and 214D. Respective end portions on the longitudinal direction LD inward side of the hot-melt adhesives 214A, 214B, 214C, and 214D serve as rising points for the gathers 21A and 21B, and areas between the rising points are raised during use.

In addition, the gathers 21A and 21B according to this embodiment may be formed of a spun-bond nonwoven fabric formed of a fiber configured with polypropylene as a core and polyethylene as a sheath, and with a basis weight of 22 g/m².

A size of the gathers 21A and 21B may be arbitrarily changed according to the size of the base absorbent core 2. In addition, stress of the elastic members 213A and 213B may be determined according to the thickness, number, and enlargement ratio of a thread rubber to be used; however, it may be arbitrarily changed according to the size of the base absorbent core 2. In this case, it is important to avoid loss of the feel against the skin when the gathers 21A, 21B make contact with the skin.

As illustrated in FIG. 3B, in the cross sectional shape in the width direction WD of the gathers 21A and 21B in the first embodiment, free ends of the gathers 21A and 21B are provided so as to face outward in the width direction WD of the base absorbent core 2.

More specifically, the end portions are provided so as to face outward in the width direction WD by folding over the fixed base portions of the gathers 21A, 21B inward in the width direction WD, and folding them over outward in the width direction WD at the central region of the length (height) of the gathers 21A and 21B. In this embodiment, the gathers 21A and 21B are configured by folding once, however, they are not limited thereto. For example, a substantially sigma-shaped cross-sectional shape so that a free end faces outward in the width direction WD of the base absorbent core 2 may be formed by folding back the gathers 21A and 21B three times. In addition, the gathers 21A and 21B may be provided while the free end directs inward in the width direction WD of the base absorbent core 2.

In addition, it is preferable that rise starting points of the gathers 21A, 21B of the front area FA and the rear edge side end portion of the fixing portion 4 are not at the same position in the longitudinal direction LD. More preferably, it is preferable that the rear edge 230 side end portion of the fixing portion 4 is arranged closer to the rear edge 230 side than the rise starting points of the gathers 21A and 21B. This is to prevent two forces from being attached to the same position since the rise starting points of the gathers 21A and 21B become regions to which a force to stretch the elastic members 213A and 213B is attached, and the end portion of the rear edge 230 side of the fixing portion 4 becomes a region to which a force is attached when the top absorbent core 3 is separated from the base absorbent core 2.

In addition, the back sheet 29, which is a liquid impermeable sheet, may be provided on the opposite side of the side on which the top absorbent core 3 is provided on the base absorbent core 2. Provision of the back sheet 29 which is a liquid impermeable sheet allows control so as to prevent a predetermined liquid which is not completely absorbed even in the base absorbent core 2 from being attached to underwear.

The wings 23A and 23B are formed so as to protrude outward in the width direction WD at both respective sides in the width direction WD of the absorbent article 1. The wings 23A and 23B are formed of a non-woven fabric, which forms the back sheet 29 which is a liquid impermeable sheet, and the gathers 21A and 21B, and formed so as to extend outward in the width direction WD of the base absorbent core 2. The back sheet 29 and the non-woven fabric are joined to each other using the hot-melt adhesive. As illustrated in FIG. 2, there are wing side dislocation preventing parts 25A and 25B at the underwear side surfaces of the wings 23A, 23B, respectively. It is possible to entirely fix the absorbent article 1 to the underwear by folding the wings 23A, 23B over to the underwear side, and attaching the wing side dislocation preventing parts 25A and 25B to the underwear.

A distance from the position Z to the front edge 220 or the edge part of the front side in the longitudinal direction LD may be exemplified as 110 m, for instance. In addition, similarly, a distance from the position Z to the rear edge 230 may be exemplified as 220 mm.

Here, the length in the width direction WD of the central region 20 of the base absorbent core 2 is, for example, from 70 mm to 120 mm, and preferably from 80 mm to 110 mm, excluding the wings 23A and 23B. In the first embodiment, 110 mm may be exemplified. In addition, it is desired that the length in the width direction WD of the base absorbent core 2 including the wings 23A and 23B be from 120 to 200 mm, and preferably from 140 mm to 180 mm. The length in the width direction WD including the wings 23A and 23B according to the first embodiment may be exemplified as 160 mm, for instance. It is preferable that the length in the width direction WD of the base absorbent core 2 be from 1.5 times to 7 times the width of the top absorbent portion 30, and more preferably from 2 times to 5 times.

It is desired that the length in the longitudinal direction LD of the base absorbent core 2 be, for example, from 250 to 500 mm, and preferably from 270 to 450 mm. The length in the longitudinal direction LD according to the first embodiment may be exemplified as 330 mm, for instance. In addition, it is desired that the length in the width direction WD of the base absorbent core 2 excluding the wings 23A and 23B be, for example, from 70 mm to 120 mm, and preferably from 80 mm to 110 mm.

It is possible to manufacture the absorbent article 1 by including the following procedure, for example. To begin with, for the base absorbent core 2, the surface sheet 27 and the absorbent core 28 are layered, and the compressed grooves 22 are then formed and pressed to each other through a pressure bonding process using a predetermined pattern embossed roll from the absorbent core 28 side. In addition, the base absorbent core 2 is formed by layering the liquid permeable back sheet 29 on a surface opposite from the surface sheet 27 of the absorbent core 28, and joining them using the hot-melt adhesive.

Moreover, for the top absorbent core 3, the oblong absorbent core 35, the second sheet 332, and the back sheet 34 are first provided at predetermined positions, and the top absorbent portion 30 is formed so as to be covered by the top sheet 331. Next, the handle part 40 is formed through an embossing process in an area of one of both end portions in the longitudinal direction LD not including the absorbent core 35. In addition, the hot-melt adhesive is attached to the other end side and joined so as to adhesively fold to the front area FA of the base absorbent core 2. This makes an area (joined part 47) where the top absorbent core 3 and the base absorbent core 2 are joined and a pressed part 46 to be described later serve as the fixing portion 4, and the side of the top absorbent core 3 on which the handle part 40 is formed serves as the free end 31.

In addition, a thermal process using an embossing technique is performed on an area where the free end 31 side of the top absorbent core 3, or area formed only by the top sheet 331 and the back sheet 34 and the rear edge 230 side of the base absorbent core 2, or area formed only by the surface sheet 27 and the back sheet 29, overlap, forming the temporary fixing portions 5. In addition, at the same time, a thermal process using an embossing technique is also performed on an area where the front edge 220 side of the base absorbent core 2 or area formed only by the surface sheet 27 and the back sheet 29 and the top absorbent core 3 overlap, fixing the top absorbent core 3 to the base absorbent core 2.

1.8. Mode of Use

An exemplary mode of use of the absorbent article 1 is described with reference to FIGS. 8 through 11.

To begin with, as illustrated in FIG. 8, the absorbent article 1 is in a state with the top absorbent core 3 mounted on the top surface of the base absorbent core 2. The top absorbent core 3 is provided in the longitudinal direction LD in the central region 20 of the base absorbent core 2. In addition, the top absorbent core 3 is temporarily fixed to the base absorbent core 2 by the temporary fixing portions 5 and 5. The entire absorbent article 1 is configured so as to allow deformation into an overall relaxed U shape along the curvature near the excretory part of the wearer's body.

Next, as illustrated in FIG. 9, the absorbent article 1 is provided in a crotch area of underwear. As with general absorbent articles, the wings 23A and 23B are then folded back so as to cover the provided part of the underwear. The absorbent article 1 is fixed to the underwear by the wing side dislocation-preventing parts 25A and 25B provided at the back surfaces of the wings 23A and 23B. The absorbent article 1 is lifted up with the underwear to the wearer's body side while the top absorbent core 3 is provided on the top surface of the base absorbent core 2. Here, since the top absorbent core 3 is being temporarily fixed by the temporary fixing portions 5, and the top absorbent core 3 is not separated from the base absorbent core 2 until the temporary fixing is released in an attaching process.

Subsequently, as illustrated in FIG. 10, a user inserts her hand between the wearer's body and the underwear from the back of the wearer's body, grasps the handle part 40, and lifts up the top absorbent core 3 in a direction indicated by an arrow R.

This releases the temporary fixing by the temporary fixing portions 5, resulting in the top absorbent core 3 being separated from the base absorbent core 2. The top absorbent core 3 separated from the base absorbent core 2 is shifted so as to enter the gluteal cleft starting at the fixing portion 4. In other words, the top absorbent core 3 is separated from the base absorbent core 2 when the handle part 40 which is grasped by the user is lifted up. The top absorbent core 3 then makes contact with the excretory part and is shifted so as to enter the gluteal cleft.

As illustrated in FIG. 11, the top absorbent core 3 provided so as to enter the gluteal cleft is then locked onto the surface of the base absorbent core 2 by the locking portion 37, which is provided on the free end side. Alternatively, the top absorbent core 3 is folded back and locked onto the outer surface side of the underwear or garment. This maintains the positioning state of the top absorbent core 3 adjusted by the user. More specifically, since the top absorbent core 3 makes contact with the wearer's body while a predetermined tension is kept by the fixing portion 4 and the locking portion 37, a predetermined force is always attached to the top absorbent core 3 in a wearer's body contacting direction. In other words, the top absorbent core 3 is fixed so that a state of contacting the wearer's body is maintained.

Use of a hook material having directionality as the locking portion 37 allows readjustment of the position of the top absorbent core 3, even after it is locked as mentioned above. In other words, the lock by the locking portion 37 may be disengaged to allow shifting only by the user grasping the handle part 40 from the back of the wearer's body, and pulling it to the rear edge 230 side of the base absorbent core 2. After adjustment of the position of the top absorbent core 3, it is possible to relock in the same manner as described above.

The back sheet 34 which is provided at the base absorbent core side contacting side of the top absorbent core 3 prevents leakage of menstrual blood absorbed by the top absorbent core 3. When the top absorbent core 3 is locked, the free end portion 32 side of the top absorbent core 3 protrudes further outward than the rear edge 230 of the base absorbent core 2. Since the back sheet 34 is provided in the protruding area, it is possible to prevent menstrual blood or the like from adhering to underwear even though the menstrual blood or the like flows to the free end portion 32 side of the top absorbent core 3.

Here, the top absorbent core 3 that makes contact with the excretory part and is provided so as to enter the gluteal cleft is deformed, so as to correspond to the shapes of the excretory part and the gluteal cleft.

More specifically, since the basis weight of the absorbent core 35 of the top absorbent core 3 differs according to a provided position, a region where the basis weight is lower than other regions serves as a folding starting point, and deformation occurs in conformity with the shapes of the excretory part and the gluteal clefts. More specifically, an area 357 which is formed substantially in a center in the width direction WD of the top absorbent portion 30 is provided so that the basis weight of the absorbent core 35 is lower than the surrounding area. Accordingly, the area 357 part serves as a folding starting point, and deformation into a mound occurs with the area 357 as the apex as the top absorbent core 3 is provided so as to enter the gluteal cleft.

The area 357 is formed so as to correspond to an area from the perineal area to the anus of the wearer's body when the top absorbent core 3 makes contact with the gluteal cleft. Accordingly, it is formed so that the top absorbent core 3 may penetrate to the innermost part of the gluteal cleft. In this manner, since the top absorbent core 3 deforms in conformity with the shape of the excretory part and related parts as mentioned above, the top absorbent core 3 is provided so as to tightly fit to the excretory part and related parts. The top absorbent core 3 is provided in a tight manner with the wearer's body. In other words, the top absorbent core 3 is provided so as to allow direct absorption of menstrual blood or the like by making contact with the excretory part, and to control of leakage of menstrual blood or the like flowing to the surface of the wearer's body.

In addition, the base absorbent core 2 absorbs predetermined liquid which is not completely absorbed by the top absorbent core 3 alone. Liquid which is not completely absorbed by the top absorbent core 3 is absorbed by the absorbent core 28 of the base absorbent core 2 through an area where the top absorbent core 3 and the base absorbent core 2 are in contact with each other. Predetermined liquid absorbed by the base absorbent core 2 is prevented from soaking into underwear by the liquid impermeable back sheet 29, and is retained in the absorbent core 28 of the base absorbent core 2.

Here, in the above description, a case of use while the top absorbent core 3 is separated from the base absorbent core 2 is described; however, the absorbent article 1 may be used while the top absorbent core 3 is not separated from the base absorbent core 2. In other words, use in the same mode as conventional sanitary napkins without releasing a temporary fixing by the temporary fixing portion 5 is possible. A user may select to use the absorbent article 1 with either aspect at the time of attaching.

According to this embodiment, since the top absorbent core 3 is separated from the base absorbent core 2 starting at the fixing portion 4, it may be operated independently from the base absorbent core 2. This increases the degree of freedom with which the top absorbent core 3 can move, allowing the absorbent core to make contact with the wearer's body continuously without being affected by movement of the garment to which the base absorbent core 2 is provided.

According to this embodiment, since the top absorbent core 3 and the base absorbent core 2 are fixed by the fixing portion 4, the top absorbent core 3 and the base absorbent core 2 are never completely separated. Accordingly, when the absorbent article 1 is removed from the wearer's body, attaching of the top absorbent core 3 is released only by pulling down from the wearer's body the underwear to which the base absorbent core 2 is fixed.

According to this embodiment, the top absorbent core 3 may keep the position adjusted at the time of attaching by locking the locking portion 37 to the base absorbent core 2, the underwear, or the wearer's body at the time of attaching. This allows the top absorbent core 3 to keep a state of being tightly fit to the wearer's body. Accordingly, it is possible to preferably absorb fluid such as menstrual blood or the like excreted from the excretory part, and to suppress leakage of the fluid flowing to the wearer's body.

In the present embodiment, the top absorbent core 3 can be deformed at a portion of different basis weight, due to a difference in basis weight in the absorbent core 35. More specifically, the top absorbent core 3 may be deformed in conformity with the shapes of the excretory part and the gluteal cleft. The top absorbent core 3 may be deformed so as to tightly fit to an excretory part, such as the vaginal opening or the like. In particular, by forming a low basis weight portion substantially in a center in the width direction WD of the top absorbent portion 30, the top absorbent portion can be prevented from deforming by being folded at a position other than the center in the width direction WD. Moreover, since the low basis weight region is formed at least from the perineal area to the anus in the longitudinal direction LD, the top absorbent core 3 may make contact with the innermost of the gluteal cleft, which is a region most desired to be tightly fit, suppressing flow leakage.

According to this embodiment, the temporary fixing portions 5 restrict the movement of the top absorbent core 3 until the temporary fixings by the temporary fixing portions 5 are released. Accordingly, since the absorbent core 3 is fixed at a certain position when the user adjusts the position of the top absorbent core 3, the position of the handle part 40 provided at an end portion of the absorbent core 3 may be easily ascertained.

According to this embodiment, the temporary fixing portions 5 restrict the movement of the top absorbent core 3. Therefore, the absorbent article 1 provides two ways of usage. In other words, the first way of usage allows tight fit of the top absorbent core 3 to the gluteal cleft by releasing a temporary fixing by the temporary fixing portions 5, and separating the free end 31 of the top absorbent core 3 from the base absorbent core 2. As the second way of usage, the absorbent article 1 may be used while the top absorbent core 3 remains to be temporarily fixed to the base absorbent core 2 without releasing the temporary fixing by the temporary fixing portions 5. In this manner, ways of usage of the absorbent article 1 may be arbitrarily selected by a user on the spot. This allows decrease in a user's in-house inventory because it is unnecessary to use different types of absorbent articles.

2. Other Embodiments

A second embodiment through a fifth embodiment is described with reference to FIGS. 12 through 16. The second embodiment and the third embodiment are other embodiments of temporary fixing portions 5; the fourth embodiment is another embodiment of a top absorbent portion 30; and the fifth embodiment is another aspect according to a top absorbent core 3 and a fixing portion 4. Note that in the following embodiments, descriptions of the same parts as with the first embodiment are omitted, and the same reference numerals are used in the drawings as in the first embodiment.

2.1. Second Embodiment

As illustrated in FIG. 12, an absorbent article 1A according to the second embodiment differs from the first embodiment in an aspect of temporary fixing.

A top absorbent core 3 is mounted on a central region 20 of a base absorbent core 2 along the longitudinal direction LD of the absorbent article 1A. A top absorbent portion 30 is temporarily fixed to the base absorbent core 2 by embossing along the longitudinal direction LD of both sides in the width direction WD of the top absorbent portion 30.

More specifically, for example, temporary fixing portions 5A are formed through a thermal process using dotted embossment in a region, both sides of which are formed only by a surface layer 33 along the longitudinal direction LD of the top absorbent portion 30.

The absorbent article 1A has two modes of use. As illustrated in FIG. 12, a first mode of use is that the top absorbent core 3 is temporarily fixed onto the base absorbent core 2 by temporary fixing portions 5A. In this manner, the absorbent article 1A may be attached to the wearer's body and used while it is temporarily fixed. In addition, as a second mode of use, it may be used by lifting the top absorbent core 3, which is temporarily fixed through a dotted embossing process, in the thickness direction so as to release the temporary fixing. More specifically, the temporary fixing is released by grasping a handle part 40 of the temporarily fixed top absorbent core 3 and lifting it in the thickness direction. When the temporary fixing is released, it becomes the same embodiment as the absorbent article 1 according to the first embodiment. A user of the absorbent article 1A may then select one of the ways of usage.

2.2. Third Embodiment

As illustrated in FIG. 13, an absorbent article 1B according to the third embodiment differs from the first embodiment in an aspect of temporary fixing.

The absorbent article 1B is formed by providing a top absorbent core 3 along the longitudinal direction LD in a central region 20 of a base absorbent core 2. The top absorbent core 3 is fusion joined to the base absorbent core 2 allowing pealing through a pressure bonding process such as dotted embossment of the entirety. More specifically, the entire top absorbent core 3 is subjected to a pressure bonding process so as to compress and integrate an absorbent core 35 and a surface layer 33 (not shown in the drawing). Areas subjected to the pressure bonding process serve as temporary fixing portions 5B.

An aspect of this embodiment is suitable when having an absorbent core in the central region 20. Since the top absorbent core 3 and the base absorbent core 2 tightly fit to each other in the longitudinal direction when the top absorbent core 3 is used without separating from the base absorbent core 2 due to pressure bonding the entirety, transferring a predetermined liquid absorbed by the top absorbent portion 30 to the central region 20 of the base absorbent core 2 is possible. In addition, pressure bonding of the entirety allows reduction in an entire thickness of the absorbent article 1B.

It is preferable that an absorbent core provided in the central region 20 according to this embodiment be configured with air-laid pulp. Provision of a high-density absorbent core such as an air-laid pulp allows increase in liquid transitivity from a top absorbent portion 30B.

The absorbent article 1B has two modes of use. As illustrated in FIG. 13, a first mode of use is a state in which the top absorbent core 3 is fixed to the base absorbent core 2 through pressure bonding. In this manner, the absorbent article 1B may be attached to the wearer's body and used while it is still fixed. In addition, as a second mode of use, a top absorbent core 3B fixed through pressure bonding may be used by releasing a temporary fixing by the temporary fixing portions 5B and separating thereof from the base absorbent core 2. More specifically, the temporary fixing portions 5B are released by grasping a handle part 40 of the temporarily fixed top absorbent core 3 and lifting thereof in the thickness direction. When the temporary fixing by the temporary fixing portions 5B is released, the same aspect as the absorbent article 1 according to the first embodiment is provided.

2.3. Fourth Embodiment

As illustrated in FIG. 14A to FIG. 14D, an absorbent article 1C according to the fourth embodiment differs from the first embodiment in an aspect of a top absorbent portion 30C of a top absorbent core 3C. FIG. 14A is a cross section of the top absorbent core 3C in the longitudinal direction. FIG. 14B is a lateral cross-sectional view cut along the line (i)-(i) of FIG. 14A. FIG. 14C is a lateral cross-sectional view cut along the line (ii)-(ii) of FIG. 14A. FIG. 14D is a lateral cross-sectional view cut along the line (iii)-(iii) of FIG. 14A.

As illustrated in FIG. 14C, an aspect of a top absorbent core 3C according to the fourth embodiment is that a top sheet 331C is provided on a base absorbent core 2 contacting side of the top absorbent core 3C so as to cover both sides in the width direction WD of an absorbent core 35 and a back sheet 34C.

In other words, the back sheet 34C is provided on the entire base absorbent core contacting side of the top absorbent core 3. The top sheet 331C covers the absorbent core 35 and both sides in the width direction WD of the back sheet 34C in the longitudinal direction on the base absorbent core 2 contacting side. Similarly, for both ends in the longitudinal direction LD of the top absorbent portion 30C in the longitudinal direction of the top absorbent core 3C, the top sheet 331C covers both sides of the base absorbent core 2 contacting side of the back sheet 34C. An area where the top sheet 331C and the back sheet 34C overlap is subjected to a joining process using a hot-melt adhesive, for example.

The back sheet 34C is formed of an SMS non-woven fabric to transmit menstrual blood or the like which is not completely absorbed by the top absorbent core 3 to the base absorbent core 2 side.

In addition, a handle part 40C is provided on a free end portion 32 side. More specifically, in an area of the free end portion 32 formed by only the top sheet 331C and the back sheet 34C, a handle part surface sheet 42C is provided so as to overlap with the area. In addition, a locking portion 37 is provided on the base absorbent core 2 contacting side of the handle part 40C, and may be fusion bonded and integrated with the area and the handle part surface sheet 42C through pressure bonding. Note that the locking portion 37 may be provided on the base absorbent core 2 contacting side of the top absorbent portion 30C, which is in the vicinity of a free end 31.

A liquid impermeable sheet with irregularities may be used as the handle part surface sheet 42C. If a smooth sheet such as a film or the like without irregularities is used as the handle part surface sheet 42C, feeling of discomfort may be given due to moisture when attached. Non-woven fabric configured with hydrophobic fibers such as spun lace, spun bond, melt blown, needle punch, and air through may be exemplified as a sheet material. SMS non-woven fabric is preferable in view of providing rigidity to the handle part 40.

At an end portion on the side opposite to the free end portion 32 of the top absorbent core 3C, the top sheet 331C and the back sheet 34C are adhesively folded together using a hot-melt adhesive. The end portion is a region where a fixing portion 4 which fixes the base absorbent core 2 and the top absorbent core 3C is formed.

2.4. Fifth Embodiment

As illustrated in FIGS. 15 and 16, an absorbent article 1D according to the fifth embodiment differs from the first embodiment in an aspect of a top absorbent core 3D.

For example, in an end portion 321D on the front edge 220 side in the longitudinal direction LD of a top absorbent portion 30, the top absorbent core 3D includes an elastic material 36D, which is provided between a fixing portion 4D and an end portion 321D. More specifically, as illustrated in FIG. 16, a top sheet 331, a back sheet 34, and an elastic material 36D are layered and subjected to pressure bonding in an area formed only by the top sheet 331 and the back sheet 34 in the end portion 321D. In addition, similarly, on a fixing portion 4D side, the top sheet 331D, the back sheet 34D, and the elastic material 36D used in the top absorbent portion 30 are layered and subjected to pressure bonding.

A material with a stretchability property within a range from 3% to 50%, preferably from 5% to 20% of the length from the fixing portion 4D to a locking portion 37 in the longitudinal direction is preferable as a member to form the elastic material 36D. Provision of such material allows reduction in feeling of pressure to the wearer's body.

In addition, this embodiment exemplifies that the top sheet 331D, the back sheet 34D, and the elastic material 36D are layered on the fixing portion 4D side and subjected to pressure bonding; however, it is not limited thereto. For example, only the top sheet 331D and the elastic material 36D should be subjected to pressure bonding; alternatively, a material with predetermined rigidity such as the handle part surface sheet 42C according to the fourth embodiment and an elastic material 36C should be subjected to pressure bonding.

2.5. Sixth Embodiment

As illustrated in FIGS. 17 and 18, an absorbent article 1E according to the sixth embodiment differs from the first embodiment in that a top absorbent core 3E has a width within a range from 40% to 90% of the length of a base absorbent core 2 in the width direction WD. In other words, the top absorbent core 3E is formed so that a length in the width direction WD is longer than the top absorbent core 3 according to the first embodiment.

In addition, it is preferable that an absorbent core 35E be provided on a top absorbent portion 30E so that a basis weight thereof partially differs. More specifically, as illustrated in FIG. 18A, the absorbent core 35E is separated along the longitudinal direction LD into three areas BW2, BW1, BW3 in the width direction WD. Here, the magnitude relation of the basis weights is as follows: BW2<BW1, BW3<BW1, and BW2=BW3. The closer to the periphery region, the lower the basis weights of BW2 and BW3, respectively. In addition, a countermeasure such as forming an incision, a groove, or the like in an area BW11 on the back side on the central line of the area BW1, or forming an incision, a groove, or the like on the back side near the border portion between the areas BW1 and BW2 and near the border portion between the areas BW1 and BW3 is taken. This allows easy deformation of the area BW1 into a shape further tightly fitting between labia when the position of the top absorbent core 3E in an attached state so as to tightly fit to the wearer's body by adjusting the position of a free end 31 side. In addition, thickness of the periphery regions of the areas BW2 and BW3 gradually decreases, respectively, making it easier to deform toward the groin, and allowing natural fitting to the groin across the labia. This increases the fit of the top absorbent core 3E in an attached state.

Alternatively, a configuration as illustrated in FIG. 18B may be attached. For example, the absorbent core 35E is divided along the longitudinal direction LD into five areas BW22, BW21, BW1, BW31, BW32 in the width direction WD. Here, the magnitude relation of the basis weights is as follows: BW21<BW22<BW1, BW31<BW32<BW1, BW21=BW31, and BW22=BW32. The closer to the periphery region, the lower the basis weights of BW21 and BW31, respectively. In addition, a countermeasure such as forming an incision, a groove, or the like in an area BW11 on the back side on the central line of the area BW1, or forming an incision, a groove, or the like on the back side near the border portion between the areas BW1 and BW2 and near the border portion between the areas BW1 and BW3 is taken. This allows easy deformation of the area BW1 into a shape further tightly fitting between labia when the position of the top absorbent core 3E in an attached state is adjusted so as to tightly fit to the wearer's body by adjusting the position of the free end 31 side. In addition, thickness of each of the periphery regions of the areas BW21 and BW31 decreases, allowing easy deformation thereof to the groin over the labia. A slightly high basis weight region of the areas BW22 and BW32 makes contact with the groin. Such a configuration improves the fit of the top absorbent core 3E in an attached state, and the existence of the areas BW22 and BW32 contributes to increase in feeling of security which removes anxiety of side leakage more than that shown in FIG. 18A.

According to FIGS. 18A and 18B, when the top absorbent core 3E makes contact with the gluteal cleft, a central area of the area BW1 is formed so as to correspond to an area from the perineal area to the anus of the wearer's body, allowing entrance to the innermost region of the gluteal cleft. In this manner, since the top absorbent core 3E deforms according to a shape of the excretory part and the like as described above, the top absorbent core 3E is provided so as to tightly fit to the excretory part and the like. The top absorbent core 3E is configured so as to make contact with the excretory part, provide cover to the groin, directly absorb menstrual blood or the like, and suppress menstrual blood or the like from flowing to the surface of the wearer's body.

When a length L1 in the width direction WD of a central region 20 of the base absorbent core 2 is approximately 110 mm, a length L2 in the width direction WD of the top absorbent portion 30E may be exemplified as a predetermined length from 70 mm to 80 mm. In this manner, if the top absorbent core 3 is configured so as to have a predetermined width within a range from 40% to 90%, and more preferably from 50% to 80%, of one side of the base absorbent core 2 in the width direction WD orthogonal to the longitudinal direction LD, advantages of the wide absorbent core 35E which covers the vaginal opening and the surrounding labia to the groin may be sufficiently taken.

2.6. Sixth Embodiment

As illustrated in FIG. 19A, the seventh embodiment differs from the sixth embodiment in the shape of a handle part 40G. The handle part 40G is joined to a top absorbent portion 30G of a top absorbent core 3G via a free end 31G including temporary fixing portions 5G. The handle part 40G includes a picking area 40G1 at the center in the width direction WD. The picking area 40G1 is formed so that the length (width) in the width direction WD is narrower than that of the top absorbent portion 30G. The position at which the handle part 40G is provided is the position where the picking area 40G1 of the handle part 40G overlaps the center of the top absorbent portion 30G in the width direction. In other words, the handle part 40G is provided so as to position the picking area 40G1 at the center in the width direction. The picking area 40G1 is then arranged so as to be outermost along the longitudinal direction LD at the center of the handle part 40G in the width direction. This allows a user to easily find the central region of the wide handle part 40G by picking the picking area 40G1, thereby improving ease of handling of the top absorbent core 3G.

FIG. 19B is a plan view illustrating a modified example of the handle part 40G according to the seventh embodiment. A handle part 40H is joined to a top absorbent portion 30H of a top absorbent core 3H via a free end 31H including temporary fixing portions 5H. The handle part 40H includes an opening area 40H1 at the center in the width direction WD. The opening area 40H1 is formed so that grasping widths HW1 and HW2 on either side are equal in the width direction WD of the handle part 40H. The position at which the handle part 40H is provided is the position where the opening area 40H1 of the handle part 40H overlaps the center of the top absorbent portion 30H in the width direction. This allows a wearer to easily find the central region of the wide handle part 40H even by finding the opening area 40H1 with only one finger, thereby improving ease of handling of the top absorbent core 3H. In addition, in handling the handle part 40H, there is an advantage that since both side periphery regions of the wide top absorbent portion 30H are pulled, both side periphery regions of the top absorbent portion 30H easily enter further inside along the groin.

2.7. Eighth Embodiment

FIG. 20A differs from the sixth embodiment in that leakage-preventing wall materials are provided at a top absorbent core 3J. In a surface layer 33 of the top absorbent core 3J configured as illustrated in FIG. 20A, leakage-preventing walls 501 are provided at side portions along the longitudinal direction LD of both end portions in the width direction WD of the top absorbent core 3J. The leakage-preventing walls 501 have a fold-back structure of a non-woven fabric 511 that is adhesively folded to lateral peripheries of a top sheet 331. Rising parts as side gathers are configured by providing polyurethane elastic threads 521 and 522 inside the folded back part. This strengthens side leakage-preventing performance of the top absorbent core.

In addition, as illustrated in FIG. 20B, in the surface layer 33 of the top absorbent core 3J, leakage-preventing walls 502 may be provided at side portions along the longitudinal direction LD at both end portions in the width direction WD of the top absorbent core 3J. The leakage-preventing walls 502 have a fold-back structure of a non-woven fabric 512, which includes an absorbent layer 531 being adhesively folded to lateral peripheries of a top sheet 331, and are configured assuming certain contact to the groin. This strengthens side leakage-preventing performance of the top absorbent core 3J.

2.8. Ninth Embodiment

As illustrated in FIG. 21, a ninth embodiment differs from the first embodiment in that an absorbent article 1K includes a top absorbent core group 3K configured with a first absorbent core 3AK as a central absorbent core provided substantially in a center in the width direction of a base absorbent core 2, a second absorbent core 3BK as a first lateral absorbent core, and a third absorbent core 3CK as a second lateral absorbent core.

The first absorbent core 3AK configuring the top absorbent core group 3K is layered in a central region 20 of the base absorbent core 2. The first absorbent core 3AK directly makes contact with an excretory part and the like of the wearer's body during use, and absorbs a predetermined liquid such as menstrual blood or the like. The second absorbent core 3BK and the third absorbent core 3CK each are provided along both sides of the first absorbent core 3AK, make contact with the groin, and suppress leakage of menstrual blood or the like flowing to the surface of the wearer's body.

Each of the top absorbent core group 3K is fixed to the base absorbent core 2 by a fixing portion provided at a region in the longitudinal direction LD thereof. An end portion which is not fixed by the fixing portion serves as a free end. An end portion of the first absorbent core 3AK on a front edge 220 side is fixed by a first fixing portion 4AK. An end portion of the first absorbent core 3AK on a rear edge 230 side serves as a first free end 31AK. An end portion of the second absorbent core 3BK on the rear edge 230 side is fixed by a second fixing portion 4BK. An end portion of the second absorbent core 3BK on the front edge 220 side serves as a second free end 31BK. An end portion of the third absorbent core 3CK on the rear edge 230 side is fixed by a third fixing portion 4CK. An end portion of the third absorbent core 3CK on the front edge 220 side serves as a third free end 31CK.

A first handle part 41AK is provided on the first free end 31AK side of the first absorbent core 3AK. A second handle part 41BK is provided on the second free end 31BK side of the second absorbent core 3BK. A third handle part 41CK is provided on the third free end 31CK side of the third absorbent core 3CK. Manipulation of making the first absorbent core 3AK make contact with the excretion area of the wearer's body and providing it along the gluteal cleft is performed at the back of the wearer's body. Manipulation of providing the second absorbent core 3BK and the third absorbent core 3CK along the groin, respectively, is performed on the front side of the wearer's body.

Since a configuration of the first absorbent core 3AK is the same as the top absorbent core 3 according to the first embodiment, description is thus omitted, and the second absorbent core 3BK and the third absorbent core 3CK are mainly described. The second absorbent core 3BK and the third absorbent core 3CK each are provided extending 5 mm in front of the front edge 220 of the base absorbent core 2. This allows easily grasping the respective free ends of the second absorbent core 3BK and the third absorbent core 3CK for lifting them. Moreover, it is possible to form a handle part at each of the extended areas.

The second absorbent core 3BK and the third absorbent core 3CK each are fixed on a side opposite to the first absorbent core 3AK in the longitudinal direction LD, and have a free end along the longitudinal direction LD. In other words, a second fixing portion 4BK and a third fixing portion 4CK each are provided on the rear edge 230 side in the longitudinal direction LD. The second free end 31BK and the third free end 31CK each are provided on the rear edge 220 side in the longitudinal direction LD. Accordingly, attaching operations for the second absorbent core 3BK and the third absorbent core 3CK are performed on the front side of the wearer's body.

The second absorbent core 3BK and the third absorbent core 3CK are formed so that the width thereof becomes narrower than the first absorbent core 3AK, respectively. More specifically, the widths of the second absorbent core 3BK and the third absorbent core 3CK each are 10 mm to 30 mm narrower than the width of the first absorbent core 3AK.

The second absorbent core 3BK and the third absorbent core 3CK each are formed so that the basis weight of an absorbent core 35 becomes lower than the first absorbent core 3AK. The reason is that the second absorbent core 3BK and the third absorbent core 3CK each are auxiliary absorbent bodies for the first absorbent core 3AK, and are absorbent bodies to be tightly fit along the groin. More specifically, the basis weight of each of the second absorbent core 3BK and the third absorbent core 3CK is from 50 g/mm² to 400 g/mm².

The basis weight of the second absorbent core 3BK and the third absorbent core 3CK may each be partially different as with the first absorbent core 3AK. It is preferable that the basis weight of the second absorbent core 3BK and the third absorbent core 3CK be adjusted so as to have a folding starting point which deforms in conformity with a shape of a wearer's body mainly in the longitudinal direction LD.

In an attached state, the second absorbent core 3BK and the third absorbent core 3CK are each provided along the groin and absorb fluid such as menstrual blood or the like flowing through the wearer's body. This controls leakage of liquid such as menstrual blood or the like of the absorbent article 1K.

As mentioned above, the second fixing portion 4BK is formed at the rear edge 230 in the longitudinal direction LD, or at a central region of a back area BAK. Pressure bonding parts 48aK and 48bK configuring the second fixing portion 4BK are formed so as to be parallel to each other in the longitudinal direction LD. The pressure-bonding portions 48aK and 48bK are each formed into a U shape extending to the rear edge 230 side in the longitudinal direction LD.

Similarly, the third fixing portion 4CK is formed at the rear edge 230 in the longitudinal direction LD, or a central region of the back area BA. Pressure bonding parts 49aK and 49bK configuring the third fixing portion 4CK are formed so as to be parallel to each other in the longitudinal direction LD. The pressure-bonding portions 49aK and 49bK are each formed into a U shape extending to the rear edge 230 side in the longitudinal direction LD.

The top absorbent core group 3K includes as temporary fixing portions, first temporary fixing portions 5AK and 5AK which temporarily lock the first absorbent core 3AK, a second temporary fixing portion 5BK which temporarily locks the second absorbent core 3BK, and a third temporary fixing portion 5CK which temporarily locks the third absorbent core 5CK.

In addition, the second temporary fixing portion 5BK is formed near a second free end 31BK of the second absorbent core 3BK. More specifically, the second temporary fixing portion 5BK is formed at a free end portion 32BK. The second temporary fixing portion 5BK is formed in an area formed only by a top sheet 331 and a back sheet 34 of the second absorbent core 3BK. Moreover, the second temporary fixing portion 5BK is formed near a second handle part 40BK of the second absorbent core 3BK. A force attached to the outer direction in the longitudinal direction LD of the second handle part 40BK or upper direction of FIG. 21 is directly transferred to the second temporary fixing portion 5BK. In other words, when the second handle part 40BK is shifted to the outer direction in the longitudinal direction LD or upper direction of FIG. 21, the temporarily fixed state of the second temporary fixing portion 5BK is released. As mentioned above, the second temporary fixing portion 5BK is formed into a circular shape at the center in the width direction LD of the free end portion 32BK, which is near the second handle part 40 of the second absorbent core 3BK. The second absorbent core 3BK is fixed at a point by a single second temporary fixing portion 5BK. Here, the third temporary fixing portion 5CK is formed in the same manner as the second temporary fixing portion 5BK of the third absorbent core 3CK.

To attach the absorbent article 1K, the absorbent article 1K is provided to the crotch area of the underwear, and fixed by folding back wings 23A and 23B. After the underwear with the absorbent article 1K is lifted to the wearer's body side, the position of the first absorbent core 3AK is adjusted, and locked to the surface of the base absorbent core 2, as with the top absorbent core 3 according to the first embodiment. In addition, the second handle part 40BK and the third handle part 40CK of the second absorbent core 3BK and the third absorbent core 3CK are grasped, respectively, and the second absorbent core 3BK and the third absorbent core 3CK are separated from the base absorbent core 2 and provided along the groin, respectively.

The second absorbent core 3BK and the third absorbent core 3CK provided along the groin are locked onto a surface of the base absorbent core 2 by a second engaging portion 37BK and a third engaging portion 37CK provided at free ends. This maintains the second absorbent core 3BK and the third absorbent core 3CK each in a positioning state adjusted by the user. More specifically, each of the second absorbent core 3BK and the third absorbent core 3CK, by way of the second fixing portion 4BK and the third fixing portion 4CK, and the second engaging portion 37BK and the third engaging portion 37CK, respectively, create a predetermined tension in making contact with the wearer's body; therefore, a predetermined force is always attached to each of the second absorbent core 3BK and the third absorbent core 3CK in a wearer's body contacting direction. In other words, the second absorbent core 3BK and the third absorbent core 3CK are each fixed so as to maintain the groin contacting state. Here, this operation is performed on a front side of the wearer's body.

According to the ninth embodiment, it is possible to keep a state in which the first absorbent core 3AK is tightly fitted to the excretion area, and a state in which the second absorbent core 3BK and the third absorbent core 3CK are tightly fitted to the groin. Accordingly, the first absorbent core 3AK may directly absorb fluid such as menstrual blood or the like excreted from the excretion area, and the second absorbent core 3BK and the third absorbent core 3CK may preferably absorb fluid such as menstrual blood or the like flowing through the wearer's body into a groin.

According to the ninth embodiment, the second handle part 40BK and the third handle part 40CK are each provided on the front edge 220 side, allowing manipulation of adjusting the respective positions of the second absorbent core 3BK and the third absorbent core 3CK on the front side of the wearer's body. Accordingly, ease of handling is more favorable than when adjusting the respective positions of the second absorbent core 3BK and the third absorbent core 3CK on the back side of the wearer's body. Adjustment with a slight force such as readjustment of a locked position of each engaging portion locked to a predetermined position of the base absorbent core 2 may be performed on the front side of the wearer's body. This allows preferable adjustment. In addition, the aforementioned operation may be performed in a visible state because the aforementioned operation may be performed on the front side of the wearer's body.

2.9. Tenth Embodiment

As illustrated in FIG. 22, an absorbent article 1L according to the tenth embodiment differs from the first embodiment in that a fixing portion 4 is formed on a rear edge 230 side, and a front edge 220 side which is an edge of a top absorbent core 3 when the top absorbent core 3 is mounted on a base absorbent core 2 serves as a free end 31.

More specifically, the position where the fixing portion 4 is formed is an end portion on the rear edge 230 side of a top absorbent core 30, which is a position corresponding to a region from an area formed only by a top sheet 331 to an area 353 where the basis weight of an absorbent core 35 is 200 g/m².

Temporary fixing portions 5 and 5 are formed near the free end 31 of the top absorbent core 3. In other words, the temporary fixing portions 5 and 5 are formed between a position Z and the free end 31. In addition, the temporary fixing portions 5 and 5 are formed near the front edge 220 of a central region 20 of the base absorbent core 2.

As a mode of use, the absorbent article 1L is fixed to the crotch area of the underwear, and the absorbent article 1L is then lifted to the wearer's body side. A user then inserts a hand between the body and the underwear from the front side of the wearer's body, grasps a handle part 40, releases the temporary fixing by temporary fixing portions 5, and adjusts a position where the top absorbent core 3 makes contact with the wearer's body. After the position where the top absorbent core 3 makes contact is adjusted, a locking portion 37 locks to the underwear or an arbitrary position of the base absorbent core 2.

2.10. Eleventh Embodiment

As illustrated in FIG. 23, the eleventh embodiment differs from the first embodiment in that an absorbent article 1M has a second free end 31BM provided on a front edge 220 side close to a position Z or a first position in the longitudinal direction LD, and a first free end 31AM provided on a rear edge 230 side far from the position Z in the longitudinal direction LD, while a top absorbent core 3M is attached to the wearer's body side or attaching target.

In other words, the top absorbent core 3M is fixed to a base absorbent core 2 by a first fixing portion 4AM and a second fixing portion 4BM configuring a fixing portion 4M provided at a region in the longitudinal direction LD thereof. Both end portions of the top absorbent core 3M not fixed by the fixing portion 4M serve as each of the first free end 31AM and the second free end 31BM. An end portion on the rear edge 230 side is the first free end 31AM, and an end portion on the front edge 220 side is the second free end 31BM.

The top absorbent core 3 includes a first part 3AM, a second part 3BM, and a third part 3CM. The first part 3AM is a region between the first fixing portion 4AM and the first free end 31AM. The second part 3BM is a region between the second fixing portion 4BM and the second free end 31BM. The third part 3CM is a region between the first fixing portion 4AM and the second fixing portion 4BM.

The first free end 31AM and the second free end 31BM are each formed so as to be spaced apart from the base absorbent core 2. The top absorbent core 3 is configured so that the first free end 31AM and the second free end 31BM are each formed so as to be spaced apart from each other, starting at the fixing portion 4 while being provided substantially in a center in the width direction WD of a central region 20 of the base absorbent core 2.

A first handle part 40AM is provided on the first free end 31AM side of the first part 3AM, and a second handle part 40BM is provided on the second free end 31BM side of the second part 3B. The position of the first part 3AM may be adjusted by the first handle part 40AM, and the position of the second part 3BM may be adjusted by the second handle part 40BM.

Adjustment of the position of the first free end 31AM side allows preferable adjustment of the position of the first part 3AM in an attached state. Adjustment of the position of the first part 3AM is performed on the back side of the wearer's body. In addition, adjustment of the position of the second free end 31BM side allows preferable adjustment of the position of the second part 3BM in an attached state. Adjustment of the position of the second part 3BM is performed on the front side of the wearer's body.

The third part 3CM is a region which is formed between the first fixing portion 4AM and the second fixing portion 4BM, and is not separated from the base absorbent core 2. In addition, the third part 3CM is formed so as to include the position Z. The third part 3CM is an area which is configured integrally with the base absorbent core 2, and makes contact with the excretion area.

The top absorbent core 3M is provided extending 20 mm in front of the front edge 220 of the base absorbent core 2, and 20 mm behind the rear edge 230 thereof. Extending the top absorbent core 3M from the respective outer peripheries in the longitudinal direction LD allows the first free end 31AM and the second free end 31BM each to be easily grasped. The first handle part 40AM and the second handle part 40BM are each formed in areas beneath the extensions.

As illustrated in FIG. 23, the fixing portion 4M is configured with the first fixing portion 4AM and the second fixing portion 4BM. The first fixing portion 4AM is formed on the rear edge 230 side of the position Z, and the second fixing portion 4BM is formed on the front edge 220 side of the position Z. The first fixing portion 4AM and the second fixing portion 4BM are formed sandwiching the position Z in the longitudinal direction LD.

The fixing portion 4AM and the second fixing portion 4BM are each formed through pressure bonding. More specifically, the first fixing portion 4AM and the second fixing portion 4BM may be formed through pressure bonding from the surface side of the top absorbent core 3, while the top absorbent core 3M is provided in the central region 20 of the base absorbent core 2.

The first fixing portion 4AM is a fixing portion which is formed on the rear edge 230 side, and serves as a starting point for the first part 3AM. The second fixing portion 4BM is a fixing portion which is formed on the front edge 220 side, and serves as a starting point of the second part 3BM. In addition, as mentioned above, the third part 3CM fixed to the base absorbent core 2 is formed by the first fixing portion 4AM and the second fixing portion 4BM.

As illustrated in FIG. 23, first temporary fixing portions 5AM and 5AM, and second temporary fixing portions 5BM and 5BM, are each formed on the top absorbent core 3M. The first temporary fixing portions 5AM and 5AM are formed between the first fixing portion 4AM and the first free end 31AM of the first part 3AM. In addition, the second temporary fixing portions 5BM and 5BM are formed between the second locking portion 4BM and the second free end 31BM of the second part 3BM.

More specifically, the first temporary fixing portions 5AM and 5AM are formed near the first free end 31AM. In addition, the second temporary fixing portions 5BM and 5BM are formed near the second free end 31BM. Further specifically, the first temporary fixing portions 5AM and 5AM are formed on either side in the width direction WD of the first free end portion 32AM of the first part 3AM. In addition, the second temporary fixing portions 5BM and 5BM are formed on either side in the width direction WD of the second free end portion 32BM of the second part 3BM.

As illustrated in FIG. 23, the absorbent article 1M is configured with a first locking portion 37AM and a second locking portion 37BM as locking means, and the central region 20 of the base absorbent core 2 as a to-be-locked body. The first locking portion 37AM and the second locking portion 37BM lock the first free end 31AM and the second free end 31BM of the top absorbent core 3M at predetermined positions, respectively. More specifically, the first locking portion 37AM and the second locking portion 37BM lock the first free end 31AM and the second free end 31BM of the top absorbent core 3 at a predetermined position, respectively, while they are attached to the wearer's body or the attaching target. More specifically, the first locking portion 37AM locks the first part 3AM, which is attached to the wearer's body at a predetermined position. In addition, the second locking portion 37BM locks the second part 3BM, which is attached to the wearer's body at a predetermined position.

The first locking portion 37AM and the second locking portion 37BM are provided on the respective sides of the first free end 31AM and the second free end 31BM of the top absorbent core 3, respectively. The first locking portion 37AM is provided on the base absorbent core 2 side of the top absorbent core 3M, or a back area BA. In addition, the second locking portion 37BM is provided on the base absorbent core 2 side of the top absorbent core 3M, or a front area FA.

The positions of the first locking portion 37AM and the second locking portion 37BM to be provided are adjusted according to a to-be-locked body, respectively. When the first locking portion 37AM and the second locking portion 37BM are each locked to the underwear or the garment which is provided so as to cover the absorbent article 1, the first locking portion 37AM and the second locking portion 37BM may be provided near the first free end portion 32AM and the second free end portion 32BM, or at the first handle part 40AM and the second handle part 40BM, respectively. In addition, to lock to the wearer's body, the first locking portion 37AM and the second locking portion 37BM may be provided, near the free end portions 32AM and 32BM of the top absorbent core 30M, the first handle part 40AM and the second handle part 40BM, respectively, on the body contacting side of the top absorbent core 30M.

Note that the locking portion 37M may be provided on the side of an area where an absorbent core 35M of the top absorbent portion 30M is provided and the free end portions 32AM, 32BM side. In this case, it is possible to select whether the first locking portion 37AM and the second locking portion 37BM are locked to the underwear or the wearer's body at the time of attaching. In addition, as mentioned above, the position and the number to be provided of the first locking portion 37AM and the second locking portion 37BM may each be arbitrarily adjusted. In addition, while in the above description, a configuration in which the first locking portion 37AM and the second locking portion 37BM are locked to the base absorbent core 2 is described, the first locking portion 37AM and the second locking portion 37BM may each be locked to the underwear, even in this configuration.

According to this embodiment, the top absorbent core 3M includes the first part 3AM provided on the back side of the wearer's body, and the second part 3BM provided on the front side of the wearer's body, allowing provision of an absorbent article having an absorbent core which can be provided so as to further follow the shape of the wearer's body. In addition, an absorbent article having an absorbent core capable of further following the movement of the wearer's body may be provided.

According to this embodiment, the second free end 31BM of the second part 3BM of the top absorbent core 3M is provided on the front side of the wearer's body, allowing performance of a part of attaching operation on the front side of the wearer's body. This allows performing an operation requiring light force control on the front side of the wearer's body, and performing the aforementioned operation at a position where visibility is favorable. Ease of handling is further favorable than when adjusting the position of the top absorbent core 3M on only the back side of the wearer's body.

2.11. Twelfth Embodiment

As illustrated in FIG. 24, an absorbent article 1F of the twelfth embodiment is assumed as an absorbent article 1F to be used in daytime, and differs from the sixth embodiment in the length in the longitudinal direction of a base absorbent core 2F, and a top absorbent core 3F.

The length in the longitudinal direction LD of the base absorbent core 2F is formed at 26 cm, for example. In addition, a width in the width direction WD of the base absorbent core 2F excluding wings 23A and 23B is formed at 105 mm, for example, and a total width of a central region 20 and lateral sides 21A and 21B not shown in the drawing may be 80 mm, for example. A fixing portion 4F is formed so as to be an area at a distance of 30 mm from a position Z, which is a position in which it is assumed that the excretory part of the wearer's body makes contact, to each of a front edge 220F side and a rear edge 230F side. Fixing parts 4F are provided in multiple places. The top absorbent core 3F is raised up from an average plane of the top absorbent core 3F, designating a central dotted area of a top absorbent portion 30F, which is sandwiched by the fixing portions 4F including the position Z as a high basis weight area. This improves tight fit property to the excretory part of the wearer's body and absorption performance. The top absorbent core 3F is formed so that the length in the width direction WD is 80 mm, and the length in the longitudinal direction is 4 cm longer than the length in the longitudinal direction of the base absorbent core 2, and is formed so as to extend 2 cm outward from the front edge 220F and the rear edge 230F of the base absorbent core 2F in the longitudinal direction, respectively.

Since the fixing portions 4F are provided near substantially the center in the longitudinal direction LD of the base absorbent core 2F, the top absorbent core 3F includes free ends 31F and 31f at either end in the longitudinal direction of the top absorbent core 3F. In addition, handle parts 40F and 40f are formed so as to extend outward in the longitudinal direction from the free end portions 32F and 32f. A length (width) in the width direction of the handle parts 40F and 40f is formed so as to be almost the same as the length (width) in the width direction of the top absorbent portions 30F and 30f. The free end portions 32F and 32f are temporarily fixed by pressing parts 51F and 51f, so as to restrict the movement thereof. Locking portions 37F and 37f are provided on a side opposite to the underwear or the back of each of the handle parts 40F and 40f. Fixing portions 4F are provided near the center in the width direction of the top absorbent core 3F, and not in both lateral areas. Accordingly, both entire lateral areas of the top absorbent core 3F may easily follow when the locking portions 37F and 37f are manipulated and the top absorbent core 3F is separated from the base absorbent core 2F, allowing making contact with the groin with natural deformation. This contributes to preventing side leakage.

In the aforementioned embodiments, the temporary fixing portions 5 are formed near the free end portions or near the handle part 40 through a dotted embossing process in the first embodiment, formed in both lateral areas in the longitudinal direction of the top absorbent portion 30 in the second embodiment, and formed across the entire surface of the top absorbent portion 30 in the third embodiment, and are not limited thereto. For example, it is possible to form them in a line along the longitudinal direction LD on both sides in the width direction WD of the top absorbent portion 30. In addition, the embossing shape is not limited to a dot, and an arbitrary shape is available. Moreover, a design such as a floral design or the like may be formed as with the embossing process for the handle part 40 according to the first embodiment.

While the top absorbent portion 30 and fiber of corresponding part of the base absorbent core 2 are subjected to thermal bonding using a dotted embossing member to perform an embossing process, the process method is not limited thereto. A corresponding part to be subjected to an embossing process may be formed by pin embossing penetrating through the absorbent core 35 of the top absorbent portion 30, or the absorbent core 28 of the base absorbent core 2.

In addition, in this embodiment, while the locking portion 37, which is provided at the top absorbent core 3 as a locking means to lock the base absorbent core 2 and the top absorbent core 3, and the surface sheet of the base absorbent core 2 as a to-be-locked part, are described, they are not limited thereto. For example, the to-be-locked part may be provided on the top absorbent core 3 side, and the locking portion may be provided on the base absorbent core 2 side. In addition, the to-be-locked part is not limited to the surface of the base absorbent core 2, and a sheet material provided at the surface of the base absorbent core 2 is available. Moreover, the sheet material may have a stretchability property. If the to-be-locked part is a sheet material with a stretchability property, the to-be-locked part is extended when the wearer's body or the underwear moves, serving as a buffer area preventing the locking portion 37 from being pulled down from the to-be-locked part. In addition, a hook material having directionality is described as a description of the locking portion 37; however, it is not limited thereto, and a mushroom hook material with multiple pins arrayed is available.

In this embodiment, the locking portion 37 is locked to the base absorbent core 2 in an attached state; however, it is not limited thereto, and it may be locked not only on the inside but also on the outside of the underwear or garment provided at the outside of the absorbent article 1. More specifically, while the absorbent article 1 is provided between the body as an attaching target and the underwear as a garment provided, so as to cover the wearer's body, the locking portion 37 may be locked to not only an inside but also an outside of the underwear. In this case, the locking portion 37 is provided closer to the free end 31 side than the position in a case of being locked to the aforementioned base absorbent core 2.

In this embodiment, the top absorbent core 3 includes the locking portion 37 on the surface of the base absorbent core 2, but is not limited thereto. For example, it is also acceptable for the top absorbent core 3 to not include the locking portion 37. In this case, the top absorbent core 3 is fixed so as to enter the gluteal cleft after the top absorbent core 3 is adjusted to be along the gluteal cleft.

In the aforementioned embodiments, the base absorbent core 2 includes the gathers 21A and 21B and the compressed grooves 22; however, it is not limited thereto, and it is also acceptable for the gathers 21A and 21B and the compressed grooves 22 to not be included. In addition, the base absorbent core 2 includes six compressed grooves 22 at almost even intervals in the width direction WD in the central region 20. For example, the base absorbent core 2 may include compressed grooves which are circular compressed grooves extending in the longitudinal direction or compressed grooves formed so that an area corresponding to the width direction WD of the position Z becomes hollow inward in the width direction WD, as well as a compressed groove in a gradual curve formed on the outside of an area which is formed so as to become hollow inward in the width direction WD of the compressed grooves.

In addition, in the aforementioned embodiments, as illustrated in FIG. 6, while the absorbent core 28 of the base absorbent core 2 has nondense portions 351 and 352, and different basis weight areas 353, 354, 355, 356, and 357, positions at which they are formed and basis weights are not limited thereto, and may be formed at other positions, or may have different basis weights. In addition, a basis weight of the absorbent core 28 may be the same in all areas.

Moreover, in the aforementioned embodiments, the temporary fixing portions 5 are formed by pressure bonding to the base absorbent core 2 through an embossing process, but are not limited thereto. For example, the temporary fixing portions 5 may be formed by a low-tack hot melt adhesive, such as an olefin series or sonic seal.

In addition, the base absorbent core 2 may not be limited to the aforementioned configuration, and a commercially available sanitary napkin may be used.

For the flexural recovery property, the handle part 40 as a sample was folded into two, and left for an hour in a state of a temperature of 20 degrees and a humidity of 60% while a load of 20 g/m² was attached. The load was then released, and was left for an hour in the same humidity as given above, and whether hardness of an end portion of a crease generated discomfort was indicated by points.

A feeling of holding the handle part 40 with the hands was evaluated for thickness (mm) of the handle part 40. More specifically, whether the feeling of holding when the handle part 40 was held was indicative of a favorable thickness was indicated by points. 'HMA' in the following Table 1 is an abbreviation for hot melt adhesive.

TABLE 1

| Test sample | Hardness B | Sensory | Resilience 2HB | Sensory | Thickness: Handhold feeling Thickness | Sensory | Configuration |
|---|---|---|---|---|---|---|---|
| 1 | 0.049 | D | 0.0961 | A | 0.912 | B | An air-through nonwoven fabric having a basis weight of 35 g/m² |
| 2 | 0.1943 | B | 0.439 | A | 1.78 | A | Two sheets of air-through nonwoven fabric having a basis weight of 35 g/m² laminated with HMA |
| 3 | 0.3321 | A | 0.765 | A | 3.56 | B | Four sheets of an air-through nonwoven fabric having a basis weight of 35 g/m² laminated with HMA |
| 4 | 0.3565 | A | 1.0248 | A | 1.75 | A | An air-through nonwoven fabric having a basis weight of 35 g/m² and a film having a basis weight of 23 g/m² laminated with HMA and folded into three |
| 5 | 0.4507 | A | 0.5643 | A | 0.487 | C | Two sheets of SMS nonwoven fabric having a basis weight of 35 g/m² laminated with HMA |
| 6 | 0.5685 | A | 1.0863 | A | 0.741 | B | Three sheets of SMS nonwoven fabric having a basis weight of 35 g/m² laminated with HMA |
| 7 | 0.7795 | A | 2.914 | A | 0.906 | A | Four sheets of SMS nonwoven fabric having a basis weight of 35 g/m² laminated with HMA |
| 8 | 1.0865 | B | 6.3762 | B | 1.367 | A | Six sheets of SMS nonwoven fabric having a basis weight of 35 g/m² laminated with HMA |
| 9 | 1.2719 | C | 10.7168 | D | 1.567 | A | Seven sheets of SMS nonwoven fabric having a basis weight of 35 g/m² laminated with HMA |

The shape of the entire base absorbent core 2 is not limited to a substantially rectangular shape, for example, and it may be an oblong shape such as an ellipse.

3. Working Example

A handle part 40 is formed with such a configuration as shown in the following table. Sensory evaluation for hardness (flexural rigidity), flexural recovery property, and hand-held feeling were performed.

A sensory test was performed and evaluated for hardness (flexural rigidity), flexural recovery property, and hand-held feeling for ten female participants. The test was performed for each sample in random order. The evaluation was an average of scores, on a scale of one to ten, for evaluation in each category. The evaluation was represented by A, B, C and D for an average scores of not less than 8, less than eight to not less than six, less than six to not less than four, respectively.

EVALUATION METHOD

The evaluation method of hardness was to indicate points of preferable hardness when the handle part 40 as a sample was held.

The hardness of the handle part 40 resulted in a range from 0.1 to 1.2 ($10^{-4}$N·m²/m), which was favorable. In addition, a bending recovery property of the handle part 40 resulted in 10 ($10^{-2}$N·m/m) or less, which was favorable. Moreover, results indicated that for a thickness of the handle part 40, a favorable case of the thickness was in a range from 0.5 to 4 mm.

The invention claimed is:

1. An absorbent article comprising:
    a first absorbent core;
    a second absorbent core, which is provided on a skin contacting side of the first absorbent core along a longitudinal direction of the first absorbent core;
    a permanent fixing portion, which permanently fixes the first absorbent core and the second absorbent core at a first end of the second absorbent core, wherein the second absorbent core has a second end opposite to the first end of the second absorbent core in the longitudinal direction and free of permanent attachment to the first absorbent core, and
    at least one temporary fixing portion between the permanent fixing portion and the second end, said temporary fixing portion temporarily fixing the second absorbent core to the first absorbent core, the temporary fixing portion being on a side of the second end of the second absorbent core; and a locking portion, which is provided on the side of the second end for temporarily fixing the second absorbent core to the first absorbent core, wherein when the absorbent article is attached to a garment, the locking portion is adapted to be locked on the inside of the garment, or locked on the outside of the garment by folding back the second absorbent core.

2. The absorbent article of claim 1, further comprising a front edge and a rear edge opposite to the front edge in the longitudinal direction, and a first position adapted to be in contact with an excretion area of a wearer, the first position being arranged closer to the front edge than the rear edge, wherein the permanent fixing portion is between the first position and the front edge.

3. The absorbent article of claim 1, further comprising a handle part at the second end of the second absorbent core and adapted to be held by a wearer.

4. The absorbent article of claim 1, wherein in an attached state, the locking portion locks the second end of the second absorbent core to the first absorbent core at a position which is further from an outer edge of the first absorbent article in the longitudinal direction than a position where the second absorbent core is temporarily fixed to the first absorbent core in an approximate flat plane.

5. The absorbent article of claim 1, wherein a dimension of the second absorbent core in a width direction orthogonal to the longitudinal direction is in a range from 40% to 90% of a dimension of the first absorbent core in the width direction.

6. The absorbent article of claim 5, further comprising leakage-preventing walls which are attached to the second absorbent core and extend in the longitudinal direction along both side portions of the second absorbent core opposite to each other in the width direction.

7. The absorbent article of claim 1, further comprising a first absorbent portion including the first absorbent core and having front and rear edges opposite to each other in the longitudinal direction; and a second absorbent portion including the second absorbent core and having front and rear edges opposite to each other in the longitudinal direction, wherein the first absorbent portion and the second absorbent portion are permanently fixed together at (i) a first position where the first absorbent core and the second absorbent core overlap and (ii) a second position where the first absorbent core and the second absorbent core do not overlap.

8. The absorbent article of claim 1, further comprising a first absorbent portion including the first absorbent core and having front and rear edges opposite to each other in the longitudinal direction; and a second absorbent portion including the second absorbent core and having front and rear edges opposite to each other in the longitudinal direction, wherein said front and rear edges of the second absorbent portion project in the longitudinal direction outwardly from said front and rear edges of the first absorbent portion, respectively.

9. The absorbent article of claim 1, further comprising an elastic member arranged between the permanent fixing portion and the temporary fixing portion in the longitudinal direction without extending into the second absorbent core.

10. The absorbent article of claim 1, wherein the locking portion attached to the second absorbent core is reattachably and temporarily joined to the first absorbent core and is adapted to be reattachably and temporarily joined to a wearer's body or a garment of the wearer.

11. The absorbent article of claim 1, wherein the second absorbent core includes first and second lateral absorbent cores, and a central absorbent core between the first and second lateral absorbent cores in a width direction orthogonal to the longitudinal direction, and the temporary fixing portion has a central temporary fixing portion on the central absorbent core at the side of the second end of the second absorbent core, and first and second temporary fixing portions on the first and second lateral absorbent cores, respectively, at a side of the first end opposite to the side of the second end in the longitudinal direction.

12. The absorbent article of claim 11, wherein the first and second lateral absorbent cores are permanently fixed to the first absorbent core at the side of the second end of the second absorbent core.

* * * * *